United States Patent
Mailand Hjort

(10) Patent No.: US 6,346,244 B1
(45) Date of Patent: *Feb. 12, 2002

(54) FUNGAL PROTEIN DISULFIDE ISOMERASE

(75) Inventor: Carsten Mailand Hjort, Vaerløse (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/262,666

(22) Filed: Mar. 4, 1999

Related U.S. Application Data

(62) Division of application No. 08/557,122, filed as application No. PCT/DK94/00266 on Jun. 28, 1994, now Pat. No. 5,879,664.

(30) Foreign Application Priority Data

Jun. 28, 1993 (DK) ................................................ 0768/93

(51) Int. Cl.⁷ .......................... A61K 38/43; C12N 9/02; C07H 21/04
(52) U.S. Cl. ................... 424/94.1; 424/70.2; 424/94.2; 424/94.5; 424/70.1; 424/78.02; 424/78.04; 435/183; 435/187; 435/189; 435/188; 435/233; 435/252.1; 435/252.3; 435/320.1; 435/263; 435/325; 435/210; 435/201; 435/209; 435/198; 435/192; 435/212; 435/219; 435/265; 435/264; 536/23.2; 514/12; 510/513; 510/514; 510/530; 426/556; 426/391; 426/390
(58) Field of Search ................................ 435/233, 189, 435/187, 188, 320.1, 252.3, 254.11, 198, 192, 212, 219, 325, 265, 201, 209, 264; 424/70.2, 94.1, 94.2, 94.5, 70.1, 132/210; 536/23.2; 426/556, 391, 390; 510/513, 514, 530

(56) References Cited

U.S. PATENT DOCUMENTS 4,894,340 A * 1/1990 Hammer et al. ............. 435/189
5,879,664 A * 3/1999 Hjort .......................... 424/70.2

FOREIGN PATENT DOCUMENTS

EP  0 293 793 A2  5/1988
WO  WO 93/25676  12/1993

OTHER PUBLICATIONS

Sugiyama et al., Biosci. Biotech. Biochem. vol. 57, No. 10, p.1704–1707, 1993.
Rudinger (1976) Characteristics of the amino acids as components of a peptide hormone sequence. In: Peptide Hormones. Ed. J. A. Parsons. University Park Press, Baltimore, MD. pp. 1–7, Jun. 1976.*
Ngo et al. (1994) Computational complexity, protein structure prediction, and the ILevinthal paradox. In: The Protein Folding Problem and Tertiary Structure Prediction. Eds. Merz et al. Birkhauser et al. Boston, MA. pp. 491–495, Jan. 1994.*
Thornton et al. (1995) Protein Engineering: Editorial Overview. Current Opinion in Biotechnology 6(4): 367–369, Sep. 1995.*
Wallace (1993) Understanding cytochrome c function: engineering protein structure by semisynthesis. The FASEB Journal 7: 505–515, Apr. 1993.*

* cited by examiner

Primary Examiner—Rebecca E. Prouty
Assistant Examiner—Richard Hutson
(74) Attorney, Agent, or Firm—Elias J. Lambiris

(57) ABSTRACT

The present invention relates to protein disulfide isomerases which are encoded by a nucleic acid sequence which hybridizes with (i) the DNA sequence of SEQ ID NO:1 or (ii) the DNA sequence of SEQ ID NO:2, under the following conditions: presoaking in 5×SSC and prehybridizing for 1 h at ~40° C. in a solution of 5×SSC, 5×Denhardt's solution, 50 mM sodium phosphate, pH 6.8, and 50 µg of denatured sonicated calf thymus DNA, followed by hybridization in the same solution supplemented with 50 µCi 32-P-dCTP labelled probe for 18 h at ~40° C. followed by washing three times in 2×SSC, 0.2% SDS at 40° C. for 30 minutes; and fragments thereof. The present invention also relates to DNA sequences encoding the protein disulfide isomerases, compositions comprising said protein disulfide isomerases and methods of use thereof.

30 Claims, 1 Drawing Sheet

SEQUENCE LISTING (1) GENERAL INFORMATION:

(iii) NUMBER OF SEQUENCES: 38

(2) INFORMATION FOR SEQ ID NO: 1:

(i) SEQUENCE CHARACTERISTICS:
       (A) LENGTH: 1953 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iii) ANTI-SENSE: NO (vi) ORIGINAL SOURCE:
       (A) ORGANISM: Aspergillus oryzae
       (B) STRAIN: IFO 4177

(ix) FEATURE:
       (A) NAME/KEY: CDS
       (B) LOCATION: join(71..445, 503..880, 962..1402,
           1479..1829)

(xi) SEQUENCE DESCRIPTION: SEQ ID NO: 1:

CCCTGCTGTC CCCATAGACA GTACACACGT CATCCTTTGA TATTGTCACA CTTGACAAAT       60

TCCCGACACC ATG CGG ACT TTC GCA CCT TGG ATC TTG AGC CTT CTA GGG        109

```
              Met Arg Thr Phe Ala Pro Trp Ile Leu Ser Leu Leu Gly
                1               5                  10

GCT TCT GCT GTA GCT TCT GCT GCC GAT GCG ACT GCC GAA GCT CCC TCC      157
Ala Ser Ala Val Ala Ser Ala Ala Asp Ala Thr Ala Glu Ala Pro Ser
     15              20                  25

GAT GTG GTC TCG CTC ACC GGG GAC ACA TTC GAA ACT TTC GTC AAG GAG      205
Asp Val Val Ser Leu Thr Gly Asp Thr Phe Glu Thr Phe Val Lys Glu
 30              35                  40                  45

CAT GAC CTA GTT TTG GCC GAG TTT TTT GCT CCC TGG TGT GGC CAT TGC      253
His Asp Leu Val Leu Ala Glu Phe Phe Ala Pro Trp Cys Gly His Cys
             50                  55                  60

AAG GCT CTC GCT CCG AAA TAC GAG CAG GCC GCC ACT GAG TTA AAG GAA      301
Lys Ala Leu Ala Pro Lys Tyr Glu Gln Ala Ala Thr Glu Leu Lys Glu
             65                  70                  75

AAG AAC ATT CCG CTG GTC AAG GTT GAT TGC ACC GAG GAA GAG GCT CTT      349
Lys Asn Ile Pro Leu Val Lys Val Asp Cys Thr Glu Glu Glu Ala Leu
             80                  85                  90

TGT AGG GAC CAA GGT GTT GAA GGT TAC CCC ACG CTG AAG ATT TTC CGT      397
Cys Arg Asp Gln Gly Val Glu Gly Tyr Pro Thr Leu Lys Ile Phe Arg
 95             100                 105

GGC CTT GAC GCT GTT AAG CCT TAT CAG GGA GCT CGT CAG ACC GAG GCG      445
Gly Leu Asp Ala Val Lys Pro Tyr Gln Gly Ala Arg Gln Thr Glu Ala
110             115                 120                 125

GTAAGTGTCA CCTGTTTGTT AGCCTTGCTC AAATAATATT GACCGCTAGT ATCATAG       502

ATT GTT TCA TAC ATG GTC AAG CAG TCA CTA CCT GCT GTG TCC CCT GTC      550
Ile Val Ser Tyr Met Val Lys Gln Ser Leu Pro Ala Val Ser Pro Val
                130                 135                 140

ACC CCA GAA AAC CTC GAA GAG ATC AAG ACT ATG GAC AAG ATT GTC GTT      598
Thr Pro Glu Asn Leu Glu Glu Ile Lys Thr Met Asp Lys Ile Val Val
                145                 150                 155

ATT GGT TAT ATC GCG TCT GAC GAC CAG ACT GCC AAT GAT ATA TTC ACC      646
Ile Gly Tyr Ile Ala Ser Asp Asp Gln Thr Ala Asn Asp Ile Phe Thr
            160                 165                 170

ACT TTT GCC GAG TCA CAG AGA GAC AAC TAC CTC TTC GCC GCC ACA AGT      694
Thr Phe Ala Glu Ser Gln Arg Asp Asn Tyr Leu Phe Ala Ala Thr Ser
        175                 180                 185

GAT GCA TCG ATC GCT AAG GCA GAA GGT GTT AAG CAA CCT TCG ATT GTT      742
Asp Ala Ser Ile Ala Lys Ala Glu Gly Val Lys Gln Pro Ser Ile Val
190             195                 200                 205

CTC TAT AAA GAC TTC GAT GAA AAG AAA GCT ACT TAT GAT GGA GAG ATT      790
Leu Tyr Lys Asp Phe Asp Glu Lys Lys Ala Thr Tyr Asp Gly Glu Ile
                210                 215                 220

GAA CAG GAT GCC CTC CTC AGT TGG GTC AAG ACT GCC AGT ACC CCC TTG      838
Glu Gln Asp Ala Leu Leu Ser Trp Val Lys Thr Ala Ser Thr Pro Leu
                225                 230                 235

GTG GGC GAG CTG GGC CCA GAG ACT TAC TCC GGA TAT ATA ACG              880
Val Gly Glu Leu Gly Pro Glu Thr Tyr Ser Gly Tyr Ile Thr
                240                 245                 250

GTATGTCACA AGACACAATC TCAATATCGC TTCACAACGT TTAGTAAATA ATCATGAGTT    940

TCTGACATGG GTTTGGTTAA G GCT GGC ATT CCA CTG GCG TAC ATT TTC GCC      991
                        Ala Gly Ile Pro Leu Ala Tyr Ile Phe Ala
                                        255                 260

GAA ACC AAA GAA GAG CGT GAG CAG TTC ACC GAG GAG TTC AAG TTC ATC      1039
Glu Thr Lys Glu Glu Arg Glu Gln Phe Thr Glu Glu Phe Lys Phe Ile
                265                 270                 275

GCC GAG AAA CAC AAG GGT TCC ATC AAT ATT GTC ACC ATT GAC GCC AAG      1087
Ala Glu Lys His Lys Gly Ser Ile Asn Ile Val Thr Ile Asp Ala Lys
            280                 285                 290
```

```
TTG TAC GGC GCT CAT GCA GGC AAT CTC AAC CTT GAC CCC TCC AAG TTC         1135
Leu Tyr Gly Ala His Ala Gly Asn Leu Asn Leu Asp Pro Ser Lys Phe
    295                 300                 305

CCT GCA TTC GCT ATT CAA GAC CCT GAA AAG AAC GCC AAG TAT CCT TAT         1183
Pro Ala Phe Ala Ile Gln Asp Pro Glu Lys Asn Ala Lys Tyr Pro Tyr
310                 315                 320                 325

GAC CAG TCG AAG GAA GTC AAG GCC AAG GAT ATC GGT AAA TTC ATC CAA         1231
Asp Gln Ser Lys Glu Val Lys Ala Lys Asp Ile Gly Lys Phe Ile Gln
                330                 335                 340

GAC GTT CTT GAT GAT AAA GTA GAG CCA AGC ATT AAG TCT GAG GCT ATT         1279
Asp Val Leu Asp Asp Lys Val Glu Pro Ser Ile Lys Ser Glu Ala Ile
            345                 350                 355

CCT GAG ACT CAG GAA GGT CCT GTT ACT GTT GTT GTC GCG CAT TCC TAT         1327
Pro Glu Thr Gln Glu Gly Pro Val Thr Val Val Val Ala His Ser Tyr
        360                 365                 370

AAG GAT CTC GTC CTT GAC AAC GAG AAG GAC GTC CTT CTC GAA TTT TAT         1375
Lys Asp Leu Val Leu Asp Asn Glu Lys Asp Val Leu Leu Glu Phe Tyr
    375                 380                 385

GCG CCA TGG TGC GGA CAC TGC AAG GCC  GTAAGTTTTC CCCCTCTTTC              1422
Ala Pro Trp Cys Gly His Cys Lys Ala
390                 395

TCTACAACGA ATTATATCCA CTCTCGCTTG CGAATACCTA ATTAAACCTT GAATAG           1478

CTT GCC CCG AAG TAC GAG GAA CTT GCA AGC CTT TAC AAG GAT ATT CCT         1526
Leu Ala Pro Lys Tyr Glu Glu Leu Ala Ser Leu Tyr Lys Asp Ile Pro
        400                 405                 410

GAA GTT ACC ATC GCC AAA ATT GAC GCA ACG GCC AAC GAT GTC CCC GAC         1574
Glu Val Thr Ile Ala Lys Ile Asp Ala Thr Ala Asn Asp Val Pro Asp
415                 420                 425                 430

TCC ATT ACA GGA TTT CCT ACT ATT AAG CTC TTC GCT GCC GGC GCC AAG         1622
Ser Ile Thr Gly Phe Pro Thr Ile Lys Leu Phe Ala Ala Gly Ala Lys
                435                 440                 445

GAC TCC CCA GTT GAA TAT GAA GGC TCT CGC ACG GTG GAG GAC CTC GCC         1670
Asp Ser Pro Val Glu Tyr Glu Gly Ser Arg Thr Val Glu Asp Leu Ala
            450                 455                 460

AAC TTC GTC AAG GAG AAT GGC AAG CAC AAG GTC GAT GCT CTT GAA GTT         1718
Asn Phe Val Lys Glu Asn Gly Lys His Lys Val Asp Ala Leu Glu Val
        465                 470                 475

GAT CCG AAG AAA GAA CAG GAG AGT GGC GAT GCC ACC GAG ACT CGG GCC         1766
Asp Pro Lys Lys Glu Gln Glu Ser Gly Asp Ala Thr Glu Thr Arg Ala
    480                 485                 490

GCC TCT GAC GAG ACC GAA ACT CCT GCT GCT ACT AGC GAT GAC AAG TCT         1814
Ala Ser Asp Glu Thr Glu Thr Pro Ala Ala Thr Ser Asp Asp Lys Ser
495                 500                 505                 510

GAG CAT GAT GAA TTG TAAATTTCAT TTGGCCTGAT AGTTTGATCC ATATTTATGT         1869
Glu His Asp Glu Leu
                515

GAATTCTTGT ATTCTACCAG CAGTTTGAGC AATCGCAGCT ACTTCCGGCT TAGGAAACTG       1929

TTGTTCTATC CTAGTGGGAA GCTT                                              1953

(2) INFORMATION FOR SEQ ID NO: 2:

(i) SEQUENCE CHARACTERISTICS:
        (A) LENGTH: 1547 base pairs
        (B) TYPE: nucleic acid
        (C) STRANDEDNESS: single
        (D) TOPOLOGY: linear (ii) MOLECULE TYPE: cDNA (iii) HYPOTHETICAL: NO
```

```
    (iii) ANTI-SENSE: NO (vi) ORIGINAL SOURCE:
          (A) ORGANISM: Aspergillus oryzae
          (B) STRAIN: IFO 4177

(ix) FEATURE:
          (A) NAME/KEY: CDS
          (B) LOCATION: 1..1547

(xi) SEQUENCE DESCRIPTION: SEQ ID NO: 2:

ATG CGG ACT TTC GCA CCT TGG ATC TTG AGC CTT CTA GGG GCT TCT GCT        48
Met Arg Thr Phe Ala Pro Trp Ile Leu Ser Leu Leu Gly Ala Ser Ala
 1               5                  10                  15

GTA GCT TCT GCT GCC GAT GCG ACT GCC GAA GCT CCC TCC GAT GTG GTC        96
Val Ala Ser Ala Ala Asp Ala Thr Ala Glu Ala Pro Ser Asp Val Val
             20                  25                  30

TCG CTC ACC GGG GAC ACA TTC GAA ACT TTC GTC AAG GAG CAT GAC CTA       144
Ser Leu Thr Gly Asp Thr Phe Glu Thr Phe Val Lys Glu His Asp Leu
         35                  40                  45

GTT TTG GCC GAG TTT TTT GCT CCC TGG TGT GGC CAT TGC AAG GCT CTC       192
Val Leu Ala Glu Phe Phe Ala Pro Trp Cys Gly His Cys Lys Ala Leu
 50                  55                  60

GCT CCG AAA TAC GAG CAG GCC GCC ACT GAG TTA AAG GAA AAG AAC ATT       240
Ala Pro Lys Tyr Glu Gln Ala Ala Thr Glu Leu Lys Glu Lys Asn Ile
 65                  70                  75                  80

CCG CTG GTC AAG GTT GAT TGC ACC GAG GAA GAG GCT CTT TGT AGG GAC       288
Pro Leu Val Lys Val Asp Cys Thr Glu Glu Glu Ala Leu Cys Arg Asp
                 85                  90                  95

CAA GGT GTT GAA GGT TAC CCC ACG CTG AAG ATT TTC CGT GGC CTT GAC       336
Gln Gly Val Glu Gly Tyr Pro Thr Leu Lys Ile Phe Arg Gly Leu Asp
             100                 105                 110

GCT GTT AAG CCT TAT CAG GGA GCT CGT CAG ACC GAG GCG ATT GTT TCA       384
Ala Val Lys Pro Tyr Gln Gly Ala Arg Gln Thr Glu Ala Ile Val Ser
         115                 120                 125

TAC ATG GTC AAG CAG TCA CTA CCT GCT GTG TCC CCT GTC ACC CCA GAA       432
Tyr Met Val Lys Gln Ser Leu Pro Ala Val Ser Pro Val Thr Pro Glu
 130                 135                 140

AAC CTC GAA GAG ATC AAG ACT ATG GAC AAG ATT GTC GTT ATT GGT TAT       480
Asn Leu Glu Glu Ile Lys Thr Met Asp Lys Ile Val Val Ile Gly Tyr
145                 150                 155                 160

ATC GCG TCT GAC GAC CAG ACT GCC AAT GAT ATA TTC ACC ACT TTT GCC       528
Ile Ala Ser Asp Asp Gln Thr Ala Asn Asp Ile Phe Thr Thr Phe Ala
                 165                 170                 175

GAG TCA CAG AGA GAC AAC TAC CTC TTC GCC GCC ACA AGT GAT GCA TCG       576
Glu Ser Gln Arg Asp Asn Tyr Leu Phe Ala Ala Thr Ser Asp Ala Ser
             180                 185                 190

ATC GCT AAG GCA GAA GGT GTT AAG CAA CCT TCG ATT GTT CTC TAT AAA       624
Ile Ala Lys Ala Glu Gly Val Lys Gln Pro Ser Ile Val Leu Tyr Lys
         195                 200                 205

GAC TTC GAT GAA AAG AAA GCT ACT TAT GAT GGA GAG ATT GAA CAG GAT       672
Asp Phe Asp Glu Lys Lys Ala Thr Tyr Asp Gly Glu Ile Glu Gln Asp
 210                 215                 220

GCC CTC CTC AGT TGG GTC AAG ACT GCC AGT ACC CCC TTG GTG GGC GAG       720
Ala Leu Leu Ser Trp Val Lys Thr Ala Ser Thr Pro Leu Val Gly Glu
225                 230                 235                 240

CTG GGC CCA GAG ACT TAC TCC GGA TAT ATA ACG GCT GGC ATT CCA CTG       768
Leu Gly Pro Glu Thr Tyr Ser Gly Tyr Ile Thr Ala Gly Ile Pro Leu
                 245                 250                 255

GCG TAC ATT TTC GCC GAA ACC AAA GAA GAG CGT GAG CAG TTC ACC GAG       816
Ala Tyr Ile Phe Ala Glu Thr Lys Glu Glu Arg Glu Gln Phe Thr Glu
             260                 265                 270
```

```
GAG TTC AAG TTC ATC GCC GAG AAA CAC AAG GGT TCC ATC AAT ATT GTC       864
Glu Phe Lys Phe Ile Ala Glu Lys His Lys Gly Ser Ile Asn Ile Val
            275                 280                 285

ACC ATT GAC GCC AAG TTG TAC GGC GCT CAT GCA GGC AAT CTC AAC CTT       912
Thr Ile Asp Ala Lys Leu Tyr Gly Ala His Ala Gly Asn Leu Asn Leu
        290                 295                 300

GAC CCC TCC AAG TTC CCT GCA TTC GCT ATT CAA GAC CCT GAA AAG AAC       960
Asp Pro Ser Lys Phe Pro Ala Phe Ala Ile Gln Asp Pro Glu Lys Asn
305                 310                 315                 320

GCC AAG TAT CCT TAT GAC CAG TCG AAG GAA GTC AAG GCC AAG GAT ATC      1008
Ala Lys Tyr Pro Tyr Asp Gln Ser Lys Glu Val Lys Ala Lys Asp Ile
                325                 330                 335

GGT AAA TTC ATC CAA GAC GTT CTT GAT GAT AAA GTA GAG CCA AGC ATT      1056
Gly Lys Phe Ile Gln Asp Val Leu Asp Asp Lys Val Glu Pro Ser Ile
            340                 345                 350

AAG TCT GAG GCT ATT CCT GAG ACT CAG GAA GGT CCT GTT ACT GTT GTT      1104
Lys Ser Glu Ala Ile Pro Glu Thr Gln Glu Gly Pro Val Thr Val Val
        355                 360                 365

GTC GCG CAT TCC TAT AAG GAT CTC GTC CTT GAC AAC GAG AAG GAC GTC      1152
Val Ala His Ser Tyr Lys Asp Leu Val Leu Asp Asn Glu Lys Asp Val
370                 375                 380

CTT CTC GAA TTT TAT GCG CCA TGG TGC GGA CAC TGC AAG GCC CTT GCC      1200
Leu Leu Glu Phe Tyr Ala Pro Trp Cys Gly His Cys Lys Ala Leu Ala
385                 390                 395                 400

CCG AAG TAC GAG GAA CTT GCA AGC CTT TAC AAG GAT ATT CCT GAA GTT      1248
Pro Lys Tyr Glu Glu Leu Ala Ser Leu Tyr Lys Asp Ile Pro Glu Val
                405                 410                 415

ACC ATC GCC AAA ATT GAC GCA ACG GCC AAC GAT GTC CCC GAC TCC ATT      1296
Thr Ile Ala Lys Ile Asp Ala Thr Ala Asn Asp Val Pro Asp Ser Ile
            420                 425                 430

ACA GGA TTT CCT ACT ATT AAG CTC TTC GCT GCC GGC GCC AAG GAC TCC      1344
Thr Gly Phe Pro Thr Ile Lys Leu Phe Ala Ala Gly Ala Lys Asp Ser
        435                 440                 445

CCA GTT GAA TAT GAA GGC TCT CGC ACG GTG GAG GAC CTC GCC AAC TTC      1392
Pro Val Glu Tyr Glu Gly Ser Arg Thr Val Glu Asp Leu Ala Asn Phe
450                 455                 460

GTC AAG GAG AAT GGC AAG CAC AAG GTC GAT GCT CTT GAA GTT GAT CCG      1440
Val Lys Glu Asn Gly Lys His Lys Val Asp Ala Leu Glu Val Asp Pro
465                 470                 475                 480

AAG AAA GAA CAG GAG AGT GGC GAT GCC ACC GAG ACT CGG GCC GCC TCT      1488
Lys Lys Glu Gln Glu Ser Gly Asp Ala Thr Glu Thr Arg Ala Ala Ser
                485                 490                 495

GAC GAG ACC GAA ACT CCT GCT GCT ACT AGC GAT GAC AAG TCT GAG CAT      1536
Asp Glu Thr Glu Thr Pro Ala Ala Thr Ser Asp Asp Lys Ser Glu His
            500                 505                 510

GAT GAA TTG TA                                                       1547
Asp Glu Leu
        515

(2) INFORMATION FOR SEQ ID NO: 3:

(i) SEQUENCE CHARACTERISTICS:
        (A) LENGTH: 515 amino acids
        (B) TYPE: amino acid
        (D) TOPOLOGY: linear (ii) MOLECULE TYPE: protein (xi) SEQUENCE DESCRIPTION: SEQ ID NO: 3:

Met Arg Thr Phe Ala Pro Trp Ile Leu Ser Leu Leu Gly Ala Ser Ala
1               5                   10                  15
```

-continued

```
Val Ala Ser Ala Ala Asp Ala Thr Ala Glu Ala Pro Ser Asp Val Val
            20                  25                  30
Ser Leu Thr Gly Asp Thr Phe Glu Thr Phe Val Lys Glu His Asp Leu
        35                  40                  45
Val Leu Ala Glu Phe Phe Ala Pro Trp Cys Gly His Cys Lys Ala Leu
    50                  55                  60
Ala Pro Lys Tyr Glu Gln Ala Ala Thr Glu Leu Lys Glu Lys Asn Ile
65                  70                  75                  80
Pro Leu Val Lys Val Asp Cys Thr Glu Glu Ala Leu Cys Arg Asp
                85                  90                  95
Gln Gly Val Glu Gly Tyr Pro Thr Leu Lys Ile Phe Arg Gly Leu Asp
            100                 105                 110
Ala Val Lys Pro Tyr Gln Gly Ala Arg Gln Thr Glu Ala Ile Val Ser
        115                 120                 125
Tyr Met Val Lys Gln Ser Leu Pro Ala Val Ser Pro Val Thr Pro Glu
    130                 135                 140
Asn Leu Glu Glu Ile Lys Thr Met Asp Lys Ile Val Val Ile Gly Tyr
145                 150                 155                 160
Ile Ala Ser Asp Asp Gln Thr Ala Asn Asp Ile Phe Thr Thr Phe Ala
            165                 170                 175
Glu Ser Gln Arg Asp Asn Tyr Leu Phe Ala Ala Thr Ser Asp Ala Ser
        180                 185                 190
Ile Ala Lys Ala Glu Gly Val Lys Gln Pro Ser Ile Val Leu Tyr Lys
    195                 200                 205
Asp Phe Asp Glu Lys Lys Ala Thr Tyr Asp Gly Glu Ile Glu Gln Asp
210                 215                 220
Ala Leu Leu Ser Trp Val Lys Thr Ala Ser Thr Pro Leu Val Gly Glu
225                 230                 235                 240
Leu Gly Pro Glu Thr Tyr Ser Gly Tyr Ile Thr Ala Gly Ile Pro Leu
            245                 250                 255
Ala Tyr Ile Phe Ala Glu Thr Lys Glu Glu Arg Glu Gln Phe Thr Glu
        260                 265                 270
Glu Phe Lys Phe Ile Ala Glu Lys His Lys Gly Ser Ile Asn Ile Val
    275                 280                 285
Thr Ile Asp Ala Lys Leu Tyr Gly Ala His Ala Gly Asn Leu Asn Leu
290                 295                 300
Asp Pro Ser Lys Phe Pro Ala Phe Ala Ile Gln Asp Pro Glu Lys Asn
305                 310                 315                 320
Ala Lys Tyr Pro Tyr Asp Gln Ser Lys Glu Val Lys Ala Lys Asp Ile
            325                 330                 335
Gly Lys Phe Ile Gln Asp Val Leu Asp Lys Val Glu Pro Ser Ile
        340                 345                 350
Lys Ser Glu Ala Ile Pro Glu Thr Gln Glu Gly Pro Val Thr Val Val
    355                 360                 365
Val Ala His Ser Tyr Lys Asp Leu Val Leu Asp Asn Glu Lys Asp Val
    370                 375                 380
Leu Leu Glu Phe Tyr Ala Pro Trp Cys Gly His Cys Lys Ala Leu Ala
385                 390                 395                 400
Pro Lys Tyr Glu Glu Leu Ala Ser Leu Tyr Lys Asp Ile Pro Glu Val
            405                 410                 415
Thr Ile Ala Lys Ile Asp Ala Thr Ala Asn Asp Val Pro Asp Ser Ile
        420                 425                 430
```

-continued

```
Thr Gly Phe Pro Thr Ile Lys Leu Phe Ala Ala Gly Ala Lys Asp Ser
        435                 440                 445

Pro Val Glu Tyr Glu Gly Ser Arg Thr Val Glu Asp Leu Ala Asn Phe
    450                 455                 460

Val Lys Glu Asn Gly Lys His Lys Val Asp Ala Leu Glu Val Asp Pro
465                 470                 475                 480

Lys Lys Glu Gln Glu Ser Gly Asp Ala Thr Glu Thr Arg Ala Ala Ser
                485                 490                 495

Asp Glu Thr Glu Thr Pro Ala Ala Thr Ser Asp Asp Lys Ser Glu His
            500                 505                 510

Asp Glu Leu
        515
```

(2) INFORMATION FOR SEQ ID NO: 4:

(i) SEQUENCE CHARACTERISTICS:
        (A) LENGTH: 511 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Arg Thr Phe Ala Pro Trp Ile Leu Ser Leu Leu Gly Ala Ser Ala
1               5                   10                  15

Val Ala Ser Ala Ala Asp Ala Thr Ala Glu Ala Pro Ser Asp Val Val
            20                  25                  30

Ser Leu Thr Gly Asp Thr Phe Glu Thr Phe Val Lys Glu His Asp Leu
        35                  40                  45

Val Leu Ala Glu Phe Phe Ala Pro Trp Cys Gly His Cys Lys Ala Leu
    50                  55                  60

Ala Pro Lys Tyr Glu Gln Ala Ala Thr Glu Leu Lys Glu Lys Asn Ile
65                  70                  75                  80

Pro Leu Val Lys Val Asp Cys Thr Glu Glu Ala Leu Cys Arg Asp
            85                  90                  95

Gln Gly Val Glu Gly Tyr Pro Thr Leu Lys Ile Phe Arg Gly Leu Asp
                100                 105                 110

Ala Val Lys Pro Tyr Gln Gly Ala Arg Gln Thr Glu Ala Ile Val Ser
            115                 120                 125

Tyr Met Val Lys Gln Ser Leu Pro Ala Val Ser Pro Val Thr Pro Glu
130                 135                 140

Asn Leu Glu Glu Ile Lys Thr Met Asp Lys Ile Val Val Ile Gly Tyr
145                 150                 155                 160

Ile Ala Ser Asp Asp Gln Thr Ala Asn Asp Ile Phe Thr Thr Phe Ala
                165                 170                 175

Glu Ser Gln Arg Asp Asn Tyr Leu Phe Ala Ala Thr Ser Asp Ala Ser
            180                 185                 190

Ile Ala Lys Ala Glu Gly Val Lys Gln Pro Ser Ile Val Leu Tyr Lys
        195                 200                 205

Asp Phe Asp Glu Lys Lys Ala Thr Tyr Asp Gly Glu Ile Glu Gln Asp
    210                 215                 220

Ala Leu Leu Ser Trp Val Lys Thr Ala Ser Thr Pro Leu Val Gly Glu
225                 230                 235                 240

Leu Gly Pro Glu Thr Tyr Ser Gly Tyr Ile Thr Ala Gly Ile Pro Leu
                245                 250                 255

Ala Tyr Ile Phe Ala Glu Thr Lys Glu Glu Arg Glu Gln Phe Thr Glu
```

-continued

```
                    260                 265                 270
Glu Phe Lys Phe Ile Ala Glu Lys His Lys Gly Ser Ile Asn Ile Val
            275                 280                 285
Thr Ile Asp Ala Lys Leu Tyr Gly Ala His Ala Gly Asn Leu Asn Leu
            290                 295                 300
Asp Pro Ser Lys Phe Pro Ala Phe Ala Ile Gln Asp Pro Glu Lys Asn
305                 310                 315                 320
Ala Lys Tyr Pro Tyr Asp Gln Ser Lys Glu Val Lys Ala Lys Asp Ile
            325                 330                 335
Gly Lys Phe Ile Gln Asp Val Leu Asp Asp Lys Val Glu Pro Ser Ile
            340                 345                 350
Lys Ser Glu Ala Ile Pro Glu Thr Gln Glu Gly Pro Val Thr Val Val
            355                 360                 365
Val Ala His Ser Tyr Lys Asp Leu Val Leu Asp Asn Glu Lys Asp Val
            370                 375                 380
Leu Leu Glu Phe Tyr Ala Pro Trp Cys Gly His Cys Lys Ala Leu Ala
385                 390                 395                 400
Pro Lys Tyr Glu Glu Leu Ala Ser Leu Tyr Lys Asp Ile Pro Glu Val
            405                 410                 415
Thr Ile Ala Lys Ile Asp Ala Thr Ala Asn Asp Val Pro Asp Ser Ile
            420                 425                 430
Thr Gly Phe Pro Thr Ile Lys Leu Phe Ala Ala Gly Ala Lys Asp Ser
            435                 440                 445
Pro Val Glu Tyr Glu Gly Ser Arg Thr Val Glu Asp Leu Ala Asn Phe
            450                 455                 460
Val Lys Glu Asn Gly Lys His Lys Val Asp Ala Leu Glu Val Asp Pro
465                 470                 475                 480
Lys Lys Glu Gln Glu Ser Gly Asp Ala Thr Glu Thr Arg Ala Ala Ser
            485                 490                 495
Asp Glu Thr Glu Thr Pro Ala Ala Thr Ser Asp Asp Lys Ser Ala
            500                 505                 510

(2) INFORMATION FOR SEQ ID NO: 5:

(i) SEQUENCE CHARACTERISTICS:
        (A) LENGTH: 281 amino acids
        (B) TYPE: amino acid
        (D) TOPOLOGY: linear (ii) MOLECULE TYPE: protein (xi) SEQUENCE DESCRIPTION: SEQ ID NO: 5:

Met Arg Thr Phe Ala Pro Trp Ile Leu Ser Leu Leu Gly Ala Ser Ala
1               5                   10                  15
Val Ala Ser Ala Ala Asp Ala Thr Ala Glu Ala Pro Ser Asp Val Val
            20                  25                  30
Ser Leu Thr Gly Asp Thr Phe Glu Thr Phe Val Lys Glu His Asp Leu
            35                  40                  45
Val Leu Ala Glu Phe Phe Ala Pro Trp Cys Gly His Cys Lys Ala Leu
            50                  55                  60
Ala Pro Lys Tyr Glu Gln Ala Ala Thr Glu Leu Lys Glu Lys Asn Ile
65                  70                  75                  80
Pro Leu Val Lys Val Asp Cys Thr Glu Glu Ala Leu Cys Arg Asp
            85                  90                  95
Gln Gly Val Glu Gly Tyr Pro Thr Leu Lys Ile Phe Arg Gly Leu Asp
            100                 105                 110
```

Ala Val Lys Pro Tyr Gln Gly Ala Arg Gln Thr Glu Ala Ile Val Ser
            115                 120                 125

Tyr Met Val Lys Gln Ser Leu Pro Ala Val Ser Pro Val Thr Pro Glu
130                 135                 140

Asn Leu Glu Glu Ile Lys Thr Met Asp Lys Ile Val Val Ile Gly Tyr
145                 150                 155                 160

Ile Ala Ser Asp Asp Gln Thr Ala Asn Asp Ile Phe Thr Thr Phe Ala
                165                 170                 175

Glu Ser Gln Arg Asp Asn Tyr Leu Phe Ala Ala Thr Ser Asp Ala Ser
            180                 185                 190

Ile Ala Lys Ala Glu Gly Val Lys Gln Pro Ser Ile Val Leu Tyr Lys
            195                 200                 205

Asp Phe Asp Glu Lys Lys Ala Thr Tyr Asp Gly Glu Ile Glu Gln Asp
            210                 215                 220

Ala Leu Leu Ser Trp Val Lys Thr Ala Ser Thr Pro Leu Val Gly Glu
225                 230                 235                 240

Leu Gly Pro Glu Thr Tyr Ser Gly Tyr Ile Thr Ala Gly Ile Pro Leu
                245                 250                 255

Ala Tyr Ile Phe Ala Glu Thr Lys Glu Glu Arg Glu Gln Phe Thr Glu
            260                 265                 270

Glu Phe Lys Phe Ile Ala Glu Lys His
            275                 280

(2) INFORMATION FOR SEQ ID NO: 6:

(i) SEQUENCE CHARACTERISTICS:
        (A) LENGTH: 174 amino acids
        (B) TYPE: amino acid
        (D) TOPOLOGY: linear (ii) MOLECULE TYPE: protein (xi) SEQUENCE DESCRIPTION: SEQ ID NO: 6:

Met Arg Thr Phe Ala Pro Trp Ile Leu Ser Leu Leu Gly Ala Ser Ala
1               5                   10                  15

Val Ala Ser Ala Ala Asp Ala Thr Ala Glu Ala Pro Ser Asp Val Val
            20                  25                  30

Ser Leu Thr Gly Asp Thr Phe Glu Thr Phe Val Lys Glu His Asp Leu
            35                  40                  45

Val Leu Ala Glu Phe Phe Ala Pro Trp Cys Gly His Cys Lys Ala Leu
            50                  55                  60

Ala Pro Lys Tyr Glu Gln Ala Ala Thr Glu Leu Lys Glu Lys Asn Ile
65                  70                  75                  80

Pro Leu Val Lys Val Asp Cys Thr Glu Glu Ala Leu Cys Arg Asp
                85                  90                  95

Gln Gly Val Glu Gly Tyr Pro Thr Leu Lys Ile Phe Arg Gly Leu Asp
            100                 105                 110

Ala Val Lys Pro Tyr Gln Gly Ala Arg Gln Thr Glu Ala Ile Val Ser
            115                 120                 125

Tyr Met Val Lys Gln Ser Leu Pro Ala Val Ser Pro Val Thr Pro Glu
130                 135                 140

Asn Leu Glu Glu Ile Lys Thr Met Asp Lys Ile Val Val Ile Gly Tyr
145                 150                 155                 160

Ile Ala Ser Asp Asp Gln Thr Ala Asn Asp Ile Phe Thr Thr
                165                 170

(2) INFORMATION FOR SEQ ID NO: 7:

(i) SEQUENCE CHARACTERISTICS:
        (A) LENGTH: 163 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Arg Thr Phe Ala Pro Trp Ile Leu Ser Leu Leu Gly Ala Ser Ala
 1               5                  10                  15

Val Ala Ser Ala Ala Asp Ala Thr Ala Glu Ala Pro Ser Asp Val Val
            20                  25                  30

Ser Leu Thr Gly Asp Thr Phe Glu Thr Phe Val Lys Glu His Asp Leu
        35                  40                  45

Val Leu Ala Glu Phe Phe Ala Pro Trp Cys Gly His Cys Lys Ala Leu
50                  55                  60

Ala Pro Lys Tyr Glu Gln Ala Ala Thr Glu Leu Lys Glu Lys Asn Ile
65                  70                  75                  80

Pro Leu Val Lys Val Asp Cys Thr Glu Glu Ala Leu Cys Arg Asp
                85                  90                  95

Gln Gly Val Glu Gly Tyr Pro Thr Leu Lys Ile Phe Arg Gly Leu Asp
            100                 105                 110

Ala Val Lys Pro Tyr Gln Gly Ala Arg Gln Thr Glu Ala Ile Val Ser
        115                 120                 125

Tyr Met Val Lys Gln Ser Leu Pro Ala Val Ser Pro Val Thr Pro Glu
130                 135                 140

Asn Leu Glu Glu Ile Lys Thr Met Asp Lys Ile Val Val Ile Gly Tyr
145                 150                 155                 160

Ile Ala Ser
```

(2) INFORMATION FOR SEQ ID NO: 8:

(i) SEQUENCE CHARACTERISTICS:
        (A) LENGTH: 143 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Arg Thr Phe Ala Pro Trp Ile Leu Ser Leu Leu Gly Ala Ser Ala
 1               5                  10                  15

Val Ala Ser Ala Ala Asp Ala Thr Ala Glu Ala Pro Ser Asp Val Val
            20                  25                  30

Ser Leu Thr Gly Asp Thr Phe Glu Thr Phe Val Lys Glu His Asp Leu
        35                  40                  45

Val Leu Ala Glu Phe Phe Ala Pro Trp Cys Gly His Cys Lys Ala Leu
50                  55                  60

Ala Pro Lys Tyr Glu Gln Ala Ala Thr Glu Leu Lys Glu Lys Asn Ile
65                  70                  75                  80

Pro Leu Val Lys Val Asp Cys Thr Glu Glu Ala Leu Cys Arg Asp
                85                  90                  95

Gln Gly Val Glu Gly Tyr Pro Thr Leu Lys Ile Phe Arg Gly Leu Asp
            100                 105                 110

Ala Val Lys Pro Tyr Gln Gly Ala Arg Gln Thr Glu Ala Ile Val Ser
        115                 120                 125
```

```
Tyr Met Val Lys Gln Ser Leu Pro Ala Val Ser Pro Val Thr Pro
    130                 135                 140
```

(2) INFORMATION FOR SEQ ID NO: 9:

(i) SEQUENCE CHARACTERISTICS:
        (A) LENGTH: 141 amino acids
        (B) TYPE: amino acid
        (D) TOPOLOGY: linear (ii) MOLECULE TYPE: protein (xi) SEQUENCE DESCRIPTION: SEQ ID NO: 9:

```
Met Arg Thr Phe Ala Pro Trp Ile Leu Ser Leu Leu Gly Ala Ser Ala
 1               5                  10                  15

Val Ala Ser Ala Ala Asp Ala Thr Ala Glu Ala Pro Ser Asp Val Val
            20                  25                  30

Ser Leu Thr Gly Asp Thr Phe Glu Thr Phe Val Lys Glu His Asp Leu
        35                  40                  45

Val Leu Ala Glu Phe Phe Ala Pro Trp Cys Gly His Cys Lys Ala Leu
    50                  55                  60

Ala Pro Lys Tyr Glu Gln Ala Ala Thr Glu Leu Lys Glu Lys Asn Ile
65                  70                  75                  80

Pro Leu Val Lys Val Asp Cys Thr Glu Glu Ala Leu Cys Arg Asp
                85                  90                  95

Gln Gly Val Glu Gly Tyr Pro Thr Leu Lys Ile Phe Arg Gly Leu Asp
            100                 105                 110

Ala Val Lys Pro Tyr Gln Gly Ala Arg Gln Thr Glu Ala Ile Val Ser
        115                 120                 125

Tyr Met Val Lys Gln Ser Leu Pro Ala Val Ser Pro Val
    130                 135                 140
```

(2) INFORMATION FOR SEQ ID NO: 10:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Arg Thr Phe Ala Pro Trp Ile Leu Ser Leu Leu Gly Ala Ser Ala
 1               5                  10                  15

Val Ala Ser Ala Ala Asp Ala Thr Ala Glu Ala Pro Ser Asp Val Val
            20                  25                  30

Ser Leu Thr Gly Asp Thr Phe Glu Thr Phe Val Lys Glu His Asp Leu
        35                  40                  45

Val Leu Ala Glu Phe Phe Ala Pro Trp Cys Gly His Cys Lys Ala Leu
    50                  55                  60

Ala Pro Lys Tyr Glu Gln Ala Ala Thr Glu Leu Lys Glu Lys Asn Ile
65                  70                  75                  80

Pro Leu Val Lys Val Asp Cys Thr Glu Glu Ala Leu Cys Arg Asp
                85                  90                  95

Gln Gly Val Glu Gly Tyr Pro Thr Leu Lys Ile Phe Arg Gly Leu Asp
            100                 105                 110

Ala Val Lys Pro Tyr Gln Gly Ala Arg Gln Thr Glu Ala Ile Val Ser
        115                 120                 125
```

Tyr Met Val
    130

(2) INFORMATION FOR SEQ ID NO: 11:

(i) SEQUENCE CHARACTERISTICS:
        (A) LENGTH: 129 amino acids
        (B) TYPE: amino acid
        (D) TOPOLOGY: linear (ii) MOLECULE TYPE: protein (xi) SEQUENCE DESCRIPTION: SEQ ID NO: 11:

Met Arg Thr Phe Ala Pro Trp Ile Leu Ser Leu Leu Gly Ala Ser Ala
 1               5                  10                  15

Val Ala Ser Ala Ala Asp Ala Thr Ala Glu Ala Pro Ser Asp Val Val
            20                  25                  30

Ser Leu Thr Gly Asp Thr Phe Glu Thr Phe Val Lys Glu His Asp Leu
        35                  40                  45

Val Leu Ala Glu Phe Phe Ala Pro Trp Cys Gly His Cys Lys Ala Leu
    50                  55                  60

Ala Pro Lys Tyr Glu Gln Ala Ala Thr Glu Leu Lys Glu Lys Asn Ile
65                  70                  75                  80

Pro Leu Val Lys Val Asp Cys Thr Glu Glu Ala Leu Cys Arg Asp
                85                  90                  95

Gln Gly Val Glu Gly Tyr Pro Thr Leu Lys Ile Phe Arg Gly Leu Asp
                100                 105                 110

Ala Val Lys Leu Ile Arg Glu Leu Leu Gln Glu Leu Val Asn Lys His
            115                 120                 125

Leu (2) INFORMATION FOR SEQ ID NO: 12:

(i) SEQUENCE CHARACTERISTICS:
        (A) LENGTH: 200 amino acids
        (B) TYPE: amino acid
        (D) TOPOLOGY: linear (ii) MOLECULE TYPE: protein (xi) SEQUENCE DESCRIPTION: SEQ ID NO: 12:

Ala Glu Ala Pro Ser Asp Val Val Ser Leu Thr Gly Asp Thr Phe Glu
 1               5                  10                  15

Thr Phe Val Lys Glu His Asp Leu Val Leu Ala Glu Phe Phe Ala Pro
            20                  25                  30

Trp Cys Gly His Cys Lys Ala Leu Ala Pro Lys Tyr Glu Gln Ala Ala
        35                  40                  45

Thr Glu Leu Lys Glu Lys Asn Ile Pro Leu Val Lys Val Asp Cys Thr
    50                  55                  60

Glu Glu Ala Leu Cys Arg Asp Gln Gly Val Glu Gly Tyr Pro Thr
65                  70                  75                  80

Leu Lys Ile Phe Arg Gly Leu Asp Ala Val Lys Pro Tyr Gln Gly Ala
                85                  90                  95

Arg Gln Thr Glu Ala Ile Val Ser Tyr Met Val Lys Gln Ser Leu Pro
                100                 105                 110

Ala Val Ser Pro Val Thr Pro Glu Asn Leu Glu Glu Ile Lys Thr Met
            115                 120                 125

Asp Lys Ile Val Val Ile Gly Tyr Ile Ala Ser Asp Asp Gln Thr Ala
        130                 135                 140

```
Asn Asp Ile Phe Thr Thr Phe Ala Glu Ser Gln Arg Asp Asn Tyr Leu
145                 150                 155                 160

Phe Ala Ala Thr Ser Asp Ala Ser Ile Ala Lys Ala Glu Gly Val Lys
            165                 170                 175

Gln Pro Ser Ile Val Leu Tyr Lys Asp Phe Asp Glu Lys Lys Ala Thr
        180                 185                 190

Tyr Asp Gly Glu Ile Glu Gln Asp
        195                 200
```

(2) INFORMATION FOR SEQ ID NO: 13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: primer 4762

(iii) HYPOTHETICAL: YES (iii) ANTI-SENSE: NO (xi) SEQUENCE DESCRIPTION: SEQ ID NO: 13:

TGGAATTCTG GTGYGGNCAY TGYAA                                  25

(2) INFORMATION FOR SEQ ID NO: 14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: primer 4763

(iii) HYPOTHETICAL: YES (iii) ANTI-SENSE: NO (xi) SEQUENCE DESCRIPTION: SEQ ID NO: 14:

TGGGATCCRC ACCANGGNGC RTA                                    23

(2) INFORMATION FOR SEQ ID NO: 15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: primer 5205

(iii) HYPOTHETICAL: YES (iii) ANTI-SENSE: NO (xi) SEQUENCE DESCRIPTION: SEQ ID NO: 15:

TTCGGATCCA CCATGCGGAC TTTCGCACC                              29

(2) INFORMATION FOR SEQ ID NO: 16:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: primer 5215

(iii) HYPOTHETICAL: YES (iii) ANTI-SENSE: NO (xi) SEQUENCE DESCRIPTION: SEQ ID NO: 16:

CCAAGCTTTA GAGATGCTTG TTGACAAGCT CCTGGAGGAG CTCCCTGATA AGCTT         55

(2) INFORMATION FOR SEQ ID NO: 17:

(i) SEQUENCE CHARACTERISTICS:
           (A) LENGTH: 45 base pairs
           (B) TYPE: nucleic acid
           (C) STRANDEDNESS: single
           (D) TOPOLOGY: linear (ii) MOLECULE TYPE: primer 5397

(iii) HYPOTHETICAL: YES (iii) ANTI-SENSE: NO (xi) SEQUENCE DESCRIPTION: SEQ ID NO: 17:

CCAAGCTTTA GACCATGTAT GACACAATCG CCTCGGTCTG ACGAG                   45

(2) INFORMATION FOR SEQ ID NO: 18:

(i) SEQUENCE CHARACTERISTICS:
           (A) LENGTH: 31 base pairs
           (B) TYPE: nucleic acid
           (C) STRANDEDNESS: single
           (D) TOPOLOGY: linear (ii) MOLECULE TYPE: primer 5895

(iii) HYPOTHETICAL: YES (iii) ANTI-SENSE: NO (xi) SEQUENCE DESCRIPTION: SEQ ID NO: 18:

CCAAGCTTTA GACAGGGGAC ACAGCAGGTA G                                  31

(2) INFORMATION FOR SEQ ID NO: 19:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (ii) MOLECULE TYPE: primer 5399

(iii) HYPOTHETICAL: YES (iii) ANTI-SENSE: NO (xi) SEQUENCE DESCRIPTION: SEQ ID NO: 19:

CCAAGCTTTA TGGGGTGACA GGGGACA                                       27

(2) INFORMATION FOR SEQ ID NO: 20:

(i) SEQUENCE CHARACTERISTICS:
           (A) LENGTH: 31 base pairs
           (B) TYPE: nucleic acid
           (C) STRANDEDNESS: single
           (D) TOPOLOGY: linear (ii) MOLECULE TYPE: primer 5894

(iii) HYPOTHETICAL: YES (iii) ANTI-SENSE: NO (xi) SEQUENCE DESCRIPTION: SEQ ID NO: 20:

CCAAGCTTTA AGACGCGATA TAACCAATAA C                          31

(2) INFORMATION FOR SEQ ID NO: 21:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: primer 5893

(iii) HYPOTHETICAL: YES (iii) ANTI-SENSE: NO (xi) SEQUENCE DESCRIPTION: SEQ ID NO: 21:

CCAAGCTTTA AGTGGTGAAT ATATCATTGG C                          31

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: primer 6314

(iii) HYPOTHETICAL: YES (iii) ANTI-SENSE: NO (xi) SEQUENCE DESCRIPTION: SEQ ID NO: 22:

CCAAGCTTAG TGTTTCTCGG CGATGAACTT                             30

(2) INFORMATION FOR SEQ ID NO: 23:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: primer 5204

(iii) HYPOTHETICAL: YES (iii) ANTI-SENSE: NO (xi) SEQUENCE DESCRIPTION: SEQ ID NO: 23:

CCAAGCTTTA CGCAGACTTG TCATCGCTAG T                           31

(2) INFORMATION FOR SEQ ID NO:24:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Ala Pro Trp Cys Gly His Cys Lys
1               5

(2) INFORMATION FOR SEQ ID NO:25:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Thr Ala Glu Ala Pro Ser Asp
1               5
```

(2) INFORMATION FOR SEQ ID NO:26:

(i) SEQUENCE CHARACTERISTICS:
        (A) LENGTH: 3052 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
Met Leu Ser Arg Ala Leu Leu Cys Leu Ala Leu Ala Trp Ala Ala Arg
1               5                   10                  15

Val Gly Ala Asp Ala Leu Glu Glu Asp Asn Val Leu Val Leu Lys
            20                  25                  30

Lys Ser Asn Phe Ala Glu Ala Leu Ala Ala His Met Leu Arg Arg Ala
                35                  40                  45

Leu Leu Cys Leu Ala Leu Thr Ala Leu Phe Arg Ala Gly Ala Gly Ala
    50                  55                  60

Pro Asp Glu Glu Asp His Val Leu Val Leu His Lys Gly Asn Phe Asp
65                  70                  75                  80

Glu Ala Leu Ala Ala His Met Leu Arg Arg Ala Leu Leu Cys Leu Ala
                85                  90                  95

Val Ala Ala Leu Val Arg Ala Asp Ala Pro Glu Glu Glu Asp His Val
                100                 105                 110

Leu Val Leu Arg Lys Ser Asn Phe Ala Glu Ala Leu Ala Ala His Met
            115                 120                 125

Leu Arg Arg Ala Val Leu Cys Leu Ala Leu Ala Val Thr Ala Gly Trp
    130                 135                 140

Ala Trp Ala Ala Glu Glu Glu Asp Asn Val Leu Val Leu Lys Ser Ser
145                 150                 155                 160

Asn Phe Ala Glu Glu Leu Ala Ala His Glu Pro Leu Glu Glu Glu Asp
                165                 170                 175

Gly Val Leu Val Leu Arg Ala Ala Asn Phe Glu Gln Ala Leu Ala Ala
                180                 185                 190

His Met Lys Phe Ser Ala Gly Ala Val Leu Ser Trp Ser Ser Leu Leu
            195                 200                 205

Leu Ala Ser Ser Val Phe Ala Gln Gln Glu Ala Val Ala Pro Glu Asp
    210                 215                 220

Ser Ala Val Val Lys Leu Ala Thr Asp Ser Phe Asn Glu Tyr Ile Gln
225                 230                 235                 240

Ser His Asn Tyr Leu Leu Val Glu Phe Tyr Ala Pro Trp Cys Gly His
                245                 250                 255

Cys Lys Ala Leu Ala Pro Glu Tyr Ala Lys Ala Ala Ala Lys Leu Lys
```

-continued

```
                260                265                270
Ala Glu Gly Ser Glu Ile Arg Leu Ala Lys Val Asp Ala Thr Glu Glu
            275                280                285

Ser Asp Leu Ala Lys Tyr Leu Leu Val Glu Phe Tyr Ala Pro Trp Cys
        290                295                300

Gly His Cys Lys Ala Leu Ala Pro Glu Tyr Ala Lys Ala Ala Gly Lys
305                310                315                320

Leu Lys Ala Glu Gly Ser Glu Ile Arg Leu Ala Lys Val Asp Ala Thr
                325                330                335

Glu Glu Ser Asp Leu Ala Lys Tyr Leu Leu Val Glu Phe Tyr Ala Pro
            340                345                350

Trp Cys Gly His Cys Lys Ala Leu Ala Pro Glu Tyr Ala Lys Ala Ala
        355                360                365

Gly Lys Leu Lys Ala Glu Gly Ser Glu Ile Arg Leu Ala Lys Val Asp
370                375                380

Ala Thr Glu Glu Ser Asp Leu Ala Lys Tyr Leu Leu Val Glu Phe Tyr
385                390                395                400

Ala Pro Trp Cys Gly His Cys Lys Ala Leu Ala Pro Glu Tyr Ala Lys
            405                410                415

Ala Ala Gly Lys Leu Lys Ala Glu Gly Ser Asp Ile Arg Leu Ala Lys
        420                425                430

Val Asp Ala Thr Glu Glu Ser Asp Leu Ala Arg His Leu Leu Val Glu
            435                440                445

Phe Tyr Ala Pro Trp Cys Gly His Cys Lys Ala Leu Ala Pro Glu Tyr
        450                455                460

Ala Lys Ala Ala Ala Gln Leu Lys Ala Glu Gly Ser Glu Ile Arg Leu
465                470                475                480

Ala Lys Val Asp Ala Thr Glu Glu Ala Glu Leu Ala Asp Leu Val Leu
            485                490                495

Ala Glu Phe Phe Ala Pro Trp Cys Gly His Cys Lys Asn Met Ala Pro
        500                505                510

Glu Tyr Val Lys Ala Ala Glu Thr Leu Val Glu Lys Asn Ile Thr Leu
        515                520                525

Ala Gln Ile Asp Cys Thr Glu Asn Gln Asp Leu Cys Gln Gln Tyr Gly
530                535                540

Val Arg Gly Tyr Pro Thr Ile Lys Phe Phe Lys Asn Gly Asp Thr Ala
545                550                555                560

Ser Pro Lys Glu Tyr Thr Ala Gly Arg Glu Ala Asp Ile Val Asn
            565                570                575

Trp Leu Lys Lys Arg Thr Gly Pro Ala Ala Thr Thr Leu Ser Gln Gln
            580                585                590

Tyr Gly Val Arg Gly Tyr Pro Thr Ile Lys Phe Phe Lys Asn Gly Asp
            595                600                605

Thr Ala Ser Pro Lys Glu Tyr Thr Ala Gly Arg Glu Ala Asp Ile
        610                615                620

Val Asn Trp Leu Lys Lys Arg Thr Gly Pro Ala Ser Thr Leu Ser
625                630                635                640

Gln Gln Tyr Gly Val Arg Gly Tyr Pro Thr Ile Lys Phe Phe Arg Asn
                645                650                655

Gly Asp Thr Ala Ser Pro Lys Glu Tyr Thr Ala Gly Arg Glu Ala Asp
            660                665                670

Asp Ile Val Asn Trp Leu Lys Lys Arg Thr Gly Pro Ala Ala Thr Thr
            675                680                685
```

-continued

```
Leu Arg Gln Gln Tyr Gly Val Arg Gly Tyr Pro Thr Ile Lys Phe Phe
    690                 695                 700
Lys Asn Gly Asp Thr Ala Ser Pro Lys Glu Tyr Thr Ala Gly Arg Glu
705                 710                 715                 720
Ala Asp Asp Ile Val Asn Trp Leu Lys Lys Arg Thr Gly Pro Ala Ala
                725                 730                 735
Thr Thr Leu Ala Gln Gln Tyr Gly Val Arg Gly Tyr Pro Thr Ile Lys
            740                 745                 750
Phe Phe Arg Asn Gly Asp Lys Ala Ala Pro Arg Glu Tyr Thr Ala Gly
        755                 760                 765
Arg Glu Ala Asp Asp Ile Val Ser Trp Leu Lys Lys Arg Thr Gly Pro
770                 775                 780
Ala Ala Thr Thr Leu Thr Met Glu His Asn Ile Pro Gly Phe Pro Ser
785                 790                 795                 800
Leu Lys Ile Phe Lys Asn Ser Asp Val Asn Asn Ser Ile Asp Tyr Glu
                805                 810                 815
Gly Pro Arg Thr Ala Glu Ala Val Gln Phe Met Ile Lys Gln Ser Gln
            820                 825                 830
Pro Ala Val Ala Val Val Ala Asp Thr Ala Ala Ala Glu Ser Leu Val
        835                 840                 845
Asp Ser Ser Glu Val Thr Val Ile Gly Phe Phe Lys Asp Ala Gly Ser
850                 855                 860
Asp Ser Ala Lys Gln Phe Leu Leu Ala Ala Glu Ala Val Asp Asp Ile
865                 870                 875                 880
Pro Phe Gly Ile Thr Ser Asn Ser Asp Asp Gly Ala Ala Ala Glu Ala
                885                 890                 895
Leu Val Glu Ser Ser Glu Val Ala Val Ile Gly Phe Phe Lys Asp Met
            900                 905                 910
Glu Ser Asp Ser Ala Lys Gln Phe Phe Leu Ala Ala Glu Val Ile Asp
        915                 920                 925
Asp Ile Pro Phe Gly Ile Thr Ser Asn Ser Asp Asp Gly Ala Ala Ala
    930                 935                 940
Glu Ser Leu Val Glu Ser Ser Glu Val Ala Val Ile Gly Phe Phe Lys
945                 950                 955                 960
Asp Val Glu Ser Asp Ser Ala Lys Gln Phe Leu Gln Ala Ala Glu Ala
                965                 970                 975
Ile Asp Asp Ile Pro Phe Gly Ile Thr Ser Asn Ser Asp Ser Ala
            980                 985                 990
Ala Ala Glu Ser Leu Val Glu Ser Ser Glu Val Ala Val Ile Gly Phe
        995                 1000                1005
Phe Lys Asp Val Glu Ser Asp Ala Ala Lys Gln Phe Leu Leu Ala Ala
    1010                1015                1020
Glu Ala Thr Asp Asp Ile Pro Phe Gly Leu Thr Ala Ser Ser Asp Asp
1025                1030                1035                1040
Ala Ala Ala Ala Glu Thr Leu Val Asp Ser Ser Glu Val Val Val Ile
                1045                1050                1055
Gly Phe Phe Lys Asp Val Thr Ser Asp Ala Ala Lys Glu Phe Leu Leu
            1060                1065                1070
Ala Ala Glu Ser Val Asp Asp Ile Pro Phe Gly Ile Ser Ser Ser Ala
        1075                1080                1085
Asp Asp Leu Pro Ala Tyr Leu Ala Asn Glu Thr Phe Val Thr Pro Val
    1090                1095                1100
```

-continued

```
Ile Val Gln Ser Gly Lys Ile Asp Ala Asp Phe Asn Ala Thr Phe Tyr
1105                1110                1115                1120

Ser Met Ala Asn Lys His Phe Asn Asp Tyr Asp Phe Val Ser Ala Glu
                1125                1130                1135

Asn Ala Asp Val Phe Ser Lys Tyr Gln Leu Asp Lys Asp Gly Val Val
                1140                1145                1150

Leu Phe Lys Lys Phe Asp Glu Gly Arg Asn Asn Phe Glu Gly Glu Ile
                1155                1160                1165

Thr Lys Glu Lys Leu Leu Asp Phe Ile Lys His Asn Gln Leu Pro Leu
                1170                1175                1180

Val Ile Val Phe Ser Lys Tyr Gln Leu Asp Lys Asp Gly Val Val Leu
1185                1190                1195                1200

Phe Lys Lys Phe Asp Glu Gly Arg Asn Asn Phe Glu Gly Glu Val Thr
                1205                1210                1215

Lys Glu Lys Leu Leu Asp Phe Ile Lys His Asn Gln Leu Pro Leu Val
                1220                1225                1230

Ile Val Phe Ser Lys Tyr Gln Leu Asp Lys Asp Gly Val Val Leu Phe
                1235                1240                1245

Lys Lys Phe Asp Glu Gly Arg Asn Asn Phe Glu Gly Glu Val Thr Lys
                1250                1255                1260

Glu Asn Leu Leu Asp Phe Ile Lys His Asn Gln Leu Pro Leu Val Ile
1265                1270                1275                1280

Val Phe Ser Arg Tyr Gln Val His Gln Asp Gly Val Val Leu Phe Lys
                1285                1290                1295

Lys Phe Asp Glu Gly Arg Asn Asn Phe Glu Gly Glu Val Thr Lys Glu
                1300                1305                1310

Lys Leu Leu Asp Phe Ile Lys His Asn Gln Leu Pro Leu Val Ile Val
                1315                1320                1325

Phe Ser Lys Tyr Gln Leu Ser Gln Asp Gly Val Val Leu Phe Lys Lys
                1330                1335                1340

Phe Asp Glu Gly Arg Asn Asn Phe Glu Gly Asp Leu Thr Lys Asp Asn
1345                1350                1355                1360

Leu Leu Asn Phe Ile Lys Ser Asn Gln Leu Pro Leu Val Ile Asp Asp
                1365                1370                1375

Phe Lys Leu Ser Ile Tyr Leu Pro Ser Ala Met Asp Glu Pro Val Val
                1380                1385                1390

Tyr Asn Gly Lys Lys Ala Asp Ile Ala Asp Ala Asp Val Phe Glu Lys
                1395                1400                1405

Trp Leu Gln Val Glu Ala Leu Pro Tyr Phe Gly Glu Phe Thr Glu Gln
                1410                1415                1420

Thr Ala Pro Lys Ile Phe Gly Gly Glu Ile Lys Thr His Ile Leu Leu
1425                1430                1435                1440

Phe Leu Pro Lys Ser Val Ser Asp Tyr Asp Gly Lys Leu Ser Asn Phe
                1445                1450                1455

Lys Lys Ala Ala Glu Gly Phe Lys Gly Lys Ile Glu Phe Thr Glu Gln
                1460                1465                1470

Thr Ala Pro Lys Ile Phe Gly Gly Glu Ile Lys Thr His Ile Leu Leu
                1475                1480                1485

Phe Leu Pro Lys Ser Val Ser Asp Tyr Glu Gly Lys Leu Ser Asn Phe
                1490                1495                1500

Lys Lys Ala Ala Glu Ser Phe Lys Gly Lys Ile Glu Phe Thr Glu Gln
1505                1510                1515                1520

Thr Ala Pro Lys Ile Phe Gly Gly Glu Ile Lys Thr His Ile Leu Leu
```

-continued

```
                1525                1530                1535
Phe Leu Pro Lys Ser Val Ser Asp Tyr Asp Gly Lys Leu Ser Asn Phe
                1540                1545                1550
Lys Thr Ala Ala Glu Ser Phe Lys Gly Lys Ile Glu Phe Thr Glu Gln
        1555                1560                1565
Thr Ala Pro Lys Ile Phe Gly Gly Glu Ile Lys Thr His Ile Leu Leu
        1570                1575                1580
Phe Leu Pro Arg Ser Ala Ala Asp His Asp Gly Lys Leu Ser Gly Phe
1585                1590                1595                1600
Lys Gln Ala Ala Glu Gly Phe Lys Gly Lys Ile Glu Phe Thr Glu Gln
                1605                1610                1615
Thr Ala Pro Lys Ile Phe Gly Gly Glu Ile Lys Thr His Ile Leu Leu
        1620                1625                1630
Phe Leu Pro Lys Ser Val Ser Asp Tyr Glu Gly Lys Leu Asp Asn Phe
        1635                1640                1645
Lys Thr Ala Ala Gly Asn Phe Lys Gly Lys Ile Glu Ile Asp Gly Ser
        1650                1655                1660
Val Phe Ala Gln Tyr Val Glu Ser Gly Leu Pro Leu Gly Tyr Leu Phe
1665                1670                1675                1680
Tyr Asn Asp Glu Glu Glu Leu Glu Tyr Lys Pro Leu Phe Thr Glu
                1685                1690                1695
Leu Ala Lys Lys Asn Arg Gly Leu Phe Ile Phe Ile Asp Ser Asp His
        1700                1705                1710
Thr Asp Asn Gln Arg Ile Leu Glu Phe Phe Gly Leu Lys Lys Glu Glu
        1715                1720                1725
Cys Pro Ala Val Arg Leu Ile Thr Leu Glu Glu Met Thr Lys Tyr
        1730                1735                1740
Leu Phe Ile Phe Ile Asp Ser Asp His Thr Asp Asn Gln Arg Ile Leu
1745                1750                1755                1760
Glu Phe Phe Gly Leu Lys Lys Glu Glu Cys Pro Ala Val Arg Leu Ile
                1765                1770                1775
Thr Leu Glu Glu Glu Met Thr Lys Tyr Leu Phe Ile Phe Ile Asp Ser
        1780                1785                1790
Asp His Thr Asp Asn Gln Arg Ile Leu Glu Phe Phe Gly Leu Lys Lys
        1795                1800                1805
Glu Glu Cys Pro Ala Val Arg Leu Ile Thr Leu Glu Glu Glu Met Thr
        1810                1815                1820
Lys Tyr Leu Phe Ile Phe Ile Asp Ser Asp His Ala Asp Asn Gln Arg
1825                1830                1835                1840
Ile Leu Glu Phe Phe Gly Leu Lys Lys Glu Glu Cys Pro Ala Val Arg
                1845                1850                1855
Leu Ile Thr Leu Glu Glu Glu Met Thr Lys Tyr Leu Phe Ile Phe Ile
                1860                1865                1870
Asp Ser Asp His Ser Asp Asn Gln Arg Ile Leu Glu Phe Phe Gly Leu
        1875                1880                1885
Lys Lys Glu Glu Cys Pro Ala Val Arg Leu Ile Thr Leu Glu Glu Glu
        1890                1895                1900
Met Thr Lys Tyr Leu Met Asn Phe Val Ser Ile Asp Ala Arg Lys Phe
1905                1910                1915                1920
Gly Arg His Ala Gly Asn Leu Asn Met Lys Glu Gln Phe Pro Leu Phe
                1925                1930                1935
Ala Ile His Asp Met Thr Glu Asp Leu Lys Tyr Gly Leu Pro Gln Leu
                1940                1945                1950
```

```
Ser Glu Glu Ala Phe Lys Pro Glu Ser Asp Glu Leu Thr Ala Glu Lys
        1955                1960                1965

Ile Thr Gln Phe Cys His His Phe Leu Glu Gly Lys Ile Lys Pro His
    1970                1975                1980

Leu Met Ser Gln Glu Leu Pro Glu Asp Trp Asp Lys Gln Pro Val Lys
1985                1990                1995                2000

Val Leu Val Gly Lys Lys Pro Glu Ser Asp Glu Leu Thr Ala Glu Lys
            2005                2010                2015

Ile Thr Glu Phe Cys His Arg Phe Leu Glu Gly Lys Ile Lys Pro His
    2020                2025                2030

Leu Met Ser Gln Glu Leu Pro Asp Asp Trp Asp Lys Gln Pro Val Lys
        2035                2040                2045

Val Leu Val Gly Lys Lys Pro Glu Ser Glu Glu Leu Thr Ala Glu Arg
    2050                2055                2060

Ile Thr Glu Phe Cys His Arg Phe Leu Glu Gly Lys Ile Lys Pro His
2065                2070                2075                2080

Leu Met Ser Gln Glu Arg Ala Asp Gly Asp Trp Asp Lys Gln Pro Val
            2085                2090                2095

Lys Val Pro Val Gly Lys Lys Pro Glu Ser Asp Glu Leu Thr Ala Glu
        2100                2105                2110

Gly Ile Thr Glu Phe Cys Gln Arg Phe Leu Glu Gly Lys Ile Lys Pro
    2115                2120                2125

His Leu Met Ser Gln Glu Leu Pro Asp Glu Asp Trp Asp Arg Gln Pro
        2130                2135                2140

Val Lys Val Leu Val Gly Lys Lys Pro Glu Ser Asp Asp Leu Thr Ala
2145                2150                2155                2160

Asp Lys Ile Lys Glu Phe Cys Asn Lys Phe Leu Glu Gly Lys Ile Lys
            2165                2170                2175

Pro His Leu Met Ser Gln Asp Leu Pro Glu Asp Trp Asp Lys Gln Pro
        2180                2185                2190

Val Lys Val Leu Val Gly Lys Asp Glu Leu Ser Asp Lys Ile Val Leu
        2195                2200                2205

Glu Ser Lys Ala Ile Glu Ser Leu Asx Lys Asp Phe Leu Lys Gly Asp
2210                2215                2220

Ala Ser Pro Ile Val Lys Ser Gln Glu Ile Phe Glu Asn Gln Asp Ser
2225                2230                2235                2240

Ser Val Phe Gln Leu Val Gly Lys Asn Phe Glu Val Ala Phe Asp
            2245                2250                2255

Glu Lys Lys Asn Val Phe Val Glu Phe Tyr Ala Pro Trp Cys Gly His
        2260                2265                2270

Cys Lys Gln Leu Ala Pro Ile Trp Asp Lys Leu Gly Glu Thr Tyr Lys
        2275                2280                2285

Asp His Glu Asn Ile Ile Ile Ala Lys Asn Phe Glu Glu Val Ala Phe
        2290                2295                2300

Asp Glu Lys Lys Asn Val Phe Val Glu Phe Tyr Ala Pro Trp Cys Gly
2305                2310                2315                2320

His Cys Lys Gln Leu Ala Pro Ile Trp Asp Lys Leu Gly Glu Thr Tyr
            2325                2330                2335

Lys Asp His Glu Asn Ile Ile Ile Ala Lys Asn Phe Glu Asp Val Ala
        2340                2345                2350

Phe Asp Glu Lys Lys Asn Val Phe Val Glu Phe Tyr Ala Pro Trp Cys
            2355                2360                2365
```

-continued

```
Gly His Cys Lys Gln Leu Ala Pro Ile Trp Asp Lys Leu Gly Glu Thr
    2370                2375                2380
Tyr Lys Asp His Glu Asn Ile Ile Ala Lys Asn Phe Glu Glu Val
2385                2390                2395                2400
Ala Phe Asp Glu Lys Lys Asn Val Phe Val Glu Phe Tyr Ala Pro Trp
                2405                2410                2415
Cys Gly His Cys Lys Gln Leu Ala Pro Ile Trp Asp Lys Leu Gly Glu
            2420                2425                2430
Thr Tyr Lys Glu His Gln Asp Ile Val Ile Ala Lys Asn Phe Glu Glu
                2435                2440                2445
Val Ala Phe Asp Glu Asn Lys Asn Val Phe Val Glu Phe Tyr Ala Pro
    2450                2455                2460
Trp Cys Gly His Cys Lys Gln Leu Ala Pro Ala Trp Asp Lys Leu Gly
2465                2470                2475                2480
Pro Thr Tyr Arg Asp His Glu Asn Ile Val Ile Ala Lys Asn His Asp
                2485                2490                2495
Glu Ile Val Asn Asp Pro Lys Lys Asp Val Leu Val Leu Tyr Tyr Ala
            2500                2505                2510
Pro Trp Cys Gly His Cys Lys Arg Leu Ala Pro Thr Tyr Gln Glu Leu
        2515                2520                2525
Ala Asp Thr Tyr Ala Asn Ala Thr Ser Asp Val Leu Ile Ala Lys Met
    2530                2535                2540
Asp Ser Thr Ala Asn Glu Val Glu Ala Val Lys Val His Ser Phe Pro
2545                2550                2555                2560
Thr Leu Lys Phe Phe Pro Ala Ser Ala Asp Arg Thr Val Ile Asp Tyr
                2565                2570                2575
Asn Gly Glu Arg Thr Leu Asp Gly Phe Lys Lys Phe Leu Glu Ser Gly
            2580                2585                2590
Gly Met Asp Ser Thr Ala Asn Glu Val Glu Ala Val Lys Val His Ser
        2595                2600                2605
Phe Pro Thr Leu Lys Phe Phe Pro Ala Ser Ala Asp Arg Thr Val Ile
    2610                2615                2620
Asp Tyr Asn Gly Glu Arg Thr Leu Asp Gly Phe Lys Lys Phe Leu Glu
2625                2630                2635                2640
Ser Gly Gly Met Asp Ser Thr Ala Asn Glu Val Glu Ala Val Lys Val
                2645                2650                2655
His Ser Phe Pro Thr Leu Lys Phe Phe Pro Ala Ser Ala Asp Arg Thr
            2660                2665                2670
Val Ile Asp Tyr Asn Gly Glu Arg Thr Leu Asp Gly Phe Lys Lys Phe
        2675                2680                2685
Leu Glu Ser Gly Gly Met Asp Ser Thr Ala Asn Glu Val Glu Ala Val
    2690                2695                2700
Lys Val His Ser Phe Pro Thr Leu Lys Phe Phe Pro Ala Gly Pro Gly
2705                2710                2715                2720
Arg Thr Val Ile Asp Tyr Asn Gly Glu Arg Thr Leu Asp Gly Phe Lys
                2725                2730                2735
Lys Phe Leu Glu Ser Gly Gly Met Asp Ser Thr Ala Asn Glu Val Glu
            2740                2745                2750
Ala Val Lys Val His Ser Phe Pro Thr Leu Lys Phe Phe Pro Ala Gly
        2755                2760                2765
Ser Gly Arg Asn Val Ile Asp Tyr Asn Gly Glu Arg Thr Leu Glu Gly
    2770                2775                2780
Phe Lys Lys Phe Leu Glu Ser Gly Gly Leu Asp His Thr Glu Asn Asp
```

-continued

```
              2785                2790                2795                2800

Val Arg Gly Val Val Ile Glu Gly Tyr Pro Thr Ile Val Leu Tyr Pro
                    2805                2810                2815

Gly Gly Lys Lys Ser Glu Ser Val Val Tyr Gln Gly Ser Arg Ser Leu
                    2820                2825                2830

Asp Ser Leu Phe Asp Phe Ile Lys Glu Asn Gly Gln Asp Gly Ala Gly
                    2835                2840                2845

Asp Asn Asp Asp Leu Asp Leu Glu Glu Ala Leu Glu Pro Asp Met Glu
                    2850                2855                2860

Glu Asp Asp Gln Lys Ala Val Lys Asp Glu Leu Gln Asp Gly Ala
2865                2870                2875                2880

Gly Asp Asp Asp Leu Glu Asp Leu Glu Glu Ala Glu Glu Pro Asp
                    2885                2890                2895

Leu Glu Glu Asp Asp Gln Lys Ala Val Lys Asp Glu Leu Gln Asp
                    2900                2905                2910

Gly Ala Gly Asp Asp Asp Leu Glu Asp Leu Glu Glu Ala Glu Glu
                    2915                2920                2925

Pro Asp Met Glu Glu Asp Asp Gln Lys Ala Val Lys Asp Glu Leu
                    2930                2935                2940

Gln Asp Gly Ala Gly Asp Glu Asp Gly Leu Glu Asp Leu Glu Glu Ala
2945                2950                2955                2960

Glu Glu Pro Asp Leu Glu Glu Asp Asp Gln Lys Ala Val Arg Asp
                    2965                2970                2975

Glu Leu Gln Asp Gly Ala Ala Ala Asp Asp Asp Leu Glu Asp Leu Glu
                    2980                2985                2990

Thr Asp Glu Glu Thr Asp Leu Glu Glu Gly Asp Asp Glu Gln Lys
                    2995                3000                3005

Ile Gln Lys Asp Glu Leu His Phe Asp Val Asp Gly Lys Ala Leu Tyr
                    3010                3015                3020

Glu Glu Ala Gln Glu Lys Ala Ala Gly Glu Ala Asp Ala Asp Ala Glu
3025                3030                3035                3040

Leu Ala Asp Glu Glu Asp Ala Ile His Asp Glu Leu
                    3045                3050
```

(2) INFORMATION FOR SEQ ID NO:27:

(i) SEQUENCE CHARACTERISTICS:
        (A) LENGTH: 509 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
Met Leu Ser Arg Ala Leu Leu Cys Leu Ala Leu Ala Trp Ala Ala Arg
1               5                   10                  15

Val Gly Ala Asp Ala Leu Glu Glu Glu Asp Asn Val Leu Val Leu Lys
                20                  25                  30

Lys Ser Asn Phe Ala Glu Ala Leu Ala Ala His Asn Tyr Leu Leu Val
            35                  40                  45

Glu Phe Tyr Ala Pro Trp Cys Gly His Cys Lys Ala Leu Ala Pro Glu
        50                  55                  60

Tyr Ala Lys Ala Ala Ala Lys Leu Lys Ala Glu Gly Ser Glu Ile Arg
65                  70                  75                  80

Leu Ala Lys Val Asp Ala Thr Glu Glu Ser Asp Leu Ala Gln Gln Tyr
```

-continued

```
                85                  90                  95
Gly Val Arg Gly Tyr Pro Thr Ile Lys Phe Phe Lys Asn Gly Asp Thr
                100                 105                 110
Ala Ser Pro Lys Glu Tyr Thr Ala Gly Arg Glu Ala Asp Asp Ile Val
                115                 120                 125
Asn Trp Leu Lys Lys Arg Thr Gly Pro Ala Ala Thr Thr Leu Ser Asp
130                 135                 140
Thr Ala Ala Glu Ser Leu Val Asp Ser Ser Glu Val Thr Val Ile
145                 150                 155                 160
Gly Phe Phe Lys Asp Ala Gly Ser Asp Ser Ala Lys Gln Phe Leu Leu
                165                 170                 175
Ala Ala Glu Ala Val Asp Asp Ile Pro Phe Gly Ile Thr Ser Asn Ser
                180                 185                 190
Asp Val Phe Ser Lys Tyr Gln Leu Asp Lys Asp Gly Val Val Leu Phe
                195                 200                 205
Lys Lys Phe Asp Glu Gly Arg Asn Asn Phe Glu Gly Glu Ile Thr Lys
                210                 215                 220
Glu Lys Leu Leu Asp Phe Ile Lys His Asn Gln Leu Pro Leu Val Ile
225                 230                 235                 240
Glu Phe Thr Glu Gln Thr Ala Pro Lys Ile Phe Gly Gly Glu Ile Lys
                245                 250                 255
Thr His Ile Leu Leu Phe Leu Pro Lys Ser Val Ser Asp Tyr Asp Gly
                260                 265                 270
Lys Leu Ser Asn Phe Lys Lys Ala Glu Gly Phe Lys Gly Lys Ile
                275                 280                 285
Leu Phe Ile Phe Ile Asp Ser Asp His Thr Asp Asn Gln Arg Ile Leu
                290                 295                 300
Glu Phe Phe Gly Leu Lys Lys Glu Glu Cys Pro Ala Val Arg Leu Ile
305                 310                 315                 320
Thr Leu Glu Glu Glu Met Thr Lys Tyr Lys Pro Glu Ser Asp Glu Leu
                325                 330                 335
Thr Ala Glu Lys Ile Thr Gln Phe Cys His His Phe Leu Glu Gly Lys
                340                 345                 350
Ile Lys Pro His Leu Met Ser Gln Glu Leu Pro Glu Asp Trp Asp Lys
                355                 360                 365
Gln Pro Val Lys Val Leu Val Gly Lys Asn Phe Glu Glu Val Ala Phe
                370                 375                 380
Asp Glu Lys Lys Asn Val Phe Val Glu Phe Tyr Ala Pro Trp Cys Gly
385                 390                 395                 400
His Cys Lys Gln Leu Ala Pro Ile Trp Asp Lys Leu Gly Glu Thr Tyr
                405                 410                 415
Lys Asp His Glu Asn Ile Ile Ala Lys Met Asp Ser Thr Ala Asn
                420                 425                 430
Glu Val Glu Ala Val Lys Val His Ser Phe Pro Thr Leu Lys Phe Phe
                435                 440                 445
Pro Ala Ser Ala Asp Arg Thr Val Ile Asp Tyr Asn Gly Glu Arg Thr
                450                 455                 460
Leu Asp Gly Phe Lys Lys Phe Leu Glu Ser Gly Gly Gln Asp Gly Ala
465                 470                 475                 480
Gly Asp Asn Asp Asp Leu Asp Leu Glu Glu Ala Leu Glu Pro Asp Met
                485                 490                 495
Glu Glu Asp Asp Asp Gln Lys Ala Val Lys Asp Glu Leu
                500                 505
```

(2) INFORMATION FOR SEQ ID NO:28:

(i) SEQUENCE CHARACTERISTICS:
        (A) LENGTH: 510 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

```
Met Leu Arg Arg Ala Leu Leu Cys Leu Ala Leu Thr Ala Leu Phe Arg
 1               5                  10                  15

Ala Gly Ala Gly Ala Pro Asp Glu Glu Asp His Val Leu Val Leu His
            20                  25                  30

Lys Gly Asn Phe Asp Glu Ala Leu Ala Ala His Lys Tyr Leu Leu Val
        35                  40                  45

Glu Phe Tyr Ala Pro Trp Cys Gly His Cys Lys Ala Leu Ala Pro Glu
50                  55                  60

Tyr Ala Lys Ala Ala Gly Lys Leu Lys Ala Glu Gly Ser Glu Ile Arg
65                  70                  75                  80

Leu Ala Lys Val Asp Ala Thr Glu Glu Ser Asp Leu Ala Gln Gln Tyr
                85                  90                  95

Gly Val Arg Gly Tyr Pro Thr Ile Lys Phe Phe Lys Asn Gly Asp Thr
            100                 105                 110

Ala Ser Pro Lys Glu Tyr Thr Ala Gly Arg Glu Ala Asp Asp Ile Val
        115                 120                 125

Asn Trp Leu Lys Lys Arg Thr Gly Pro Ala Ala Ser Thr Leu Ser Asp
130                 135                 140

Gly Ala Ala Ala Glu Ala Leu Val Glu Ser Ser Glu Val Ala Val Ile
145                 150                 155                 160

Gly Phe Phe Lys Asp Met Glu Ser Asp Ser Ala Lys Gln Phe Phe Leu
                165                 170                 175

Ala Ala Glu Val Ile Asp Ile Pro Phe Gly Ile Thr Ser Asn Ser
            180                 185                 190

Asp Val Phe Ser Lys Tyr Gln Leu Asp Lys Asp Gly Val Val Leu Phe
        195                 200                 205

Lys Lys Phe Asp Glu Gly Arg Asn Asn Phe Glu Gly Glu Val Thr Lys
210                 215                 220

Glu Lys Leu Leu Asp Phe Ile Lys His Asn Gln Leu Pro Leu Val Ile
225                 230                 235                 240

Glu Phe Thr Glu Gln Thr Ala Pro Lys Ile Phe Gly Gly Glu Ile Lys
                245                 250                 255

Thr His Ile Leu Leu Phe Leu Pro Lys Ser Val Ser Asp Tyr Glu Gly
            260                 265                 270

Lys Leu Ser Asn Phe Lys Lys Ala Ala Glu Ser Phe Lys Gly Lys Ile
        275                 280                 285

Leu Phe Ile Phe Ile Asp Ser Asp His Thr Asp Asn Gln Arg Ile Leu
290                 295                 300

Glu Phe Phe Gly Leu Lys Lys Glu Glu Cys Pro Ala Val Arg Leu Ile
305                 310                 315                 320

Thr Leu Glu Glu Glu Met Thr Lys Tyr Lys Pro Glu Ser Asp Glu Leu
                325                 330                 335

Thr Ala Glu Lys Ile Thr Glu Phe Cys His Arg Phe Leu Glu Gly Lys
            340                 345                 350
```

```
Ile Lys Pro His Leu Met Ser Gln Glu Leu Pro Asp Asp Trp Asp Lys
        355                 360                 365

Gln Pro Val Lys Val Leu Val Gly Lys Asn Phe Glu Glu Val Ala Phe
        370                 375                 380

Asp Glu Lys Lys Asn Val Phe Val Glu Phe Tyr Ala Pro Trp Cys Gly
385                 390                 395                 400

His Cys Lys Gln Leu Ala Pro Ile Trp Asp Lys Leu Gly Glu Thr Tyr
                405                 410                 415

Lys Asp His Glu Asn Ile Ile Ile Ala Lys Met Asp Ser Thr Ala Asn
            420                 425                 430

Glu Val Glu Ala Val Lys Val His Ser Phe Pro Thr Leu Lys Phe Phe
        435                 440                 445

Pro Ala Ser Ala Asp Arg Thr Val Ile Asp Tyr Asn Gly Glu Arg Thr
        450                 455                 460

Leu Asp Gly Phe Lys Lys Phe Leu Glu Ser Gly Gly Gln Asp Gly Ala
465                 470                 475                 480

Gly Asp Asp Asp Leu Glu Asp Leu Glu Glu Ala Glu Glu Pro Asp
                485                 490                 495

Leu Glu Glu Asp Asp Asp Gln Lys Ala Val Lys Asp Glu Leu
        500                 505                 510

(2) INFORMATION FOR SEQ ID NO:29:

(i) SEQUENCE CHARACTERISTICS:
        (A) LENGTH: 509 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

Met Leu Arg Arg Ala Leu Leu Cys Leu Ala Val Ala Ala Leu Val Arg
1               5                   10                  15

Ala Asp Ala Pro Glu Glu Glu Asp His Val Leu Val Leu Arg Lys Ser
            20                  25                  30

Asn Phe Ala Glu Ala Leu Ala Ala His Lys Tyr Leu Leu Val Glu Phe
        35                  40                  45

Tyr Ala Pro Trp Cys Gly His Cys Lys Ala Leu Ala Pro Glu Tyr Ala
50                  55                  60

Lys Ala Ala Gly Lys Leu Lys Ala Glu Gly Ser Glu Ile Arg Leu Ala
65              70                  75                  80

Lys Val Asp Ala Thr Glu Glu Ser Asp Leu Ala Gln Gln Tyr Gly Val
                85                  90                  95

Arg Gly Tyr Pro Thr Ile Lys Phe Phe Arg Asn Gly Asp Thr Ala Ser
            100                 105                 110

Pro Lys Glu Tyr Thr Ala Gly Arg Glu Ala Asp Asp Ile Val Asn Trp
        115                 120                 125

Leu Lys Lys Arg Thr Gly Pro Ala Ala Thr Thr Leu Arg Asp Gly Ala
        130                 135                 140

Ala Ala Glu Ser Leu Val Glu Ser Ser Glu Val Ala Val Ile Gly Phe
145                 150                 155                 160

Phe Lys Asp Val Glu Ser Asp Ser Ala Lys Gln Phe Leu Gln Ala Ala
                165                 170                 175

Glu Ala Ile Asp Asp Ile Pro Phe Gly Ile Thr Ser Asn Ser Asp Val
            180                 185                 190
```

```
Phe Ser Lys Tyr Gln Leu Asp Lys Asp Gly Val Val Leu Phe Lys Lys
            195                 200                 205

Phe Asp Glu Gly Arg Asn Asn Phe Gly Glu Val Thr Lys Glu Asn
        210                 215                 220

Leu Leu Asp Phe Ile Lys His Asn Gln Leu Pro Leu Val Ile Glu Phe
225                 230                 235                 240

Thr Glu Gln Thr Ala Pro Lys Ile Phe Gly Glu Ile Lys Thr His
                245                 250                 255

Ile Leu Leu Phe Leu Pro Lys Ser Val Ser Asp Tyr Asp Gly Lys Leu
            260                 265                 270

Ser Asn Phe Lys Thr Ala Ala Glu Ser Phe Lys Gly Lys Ile Leu Phe
            275                 280                 285

Ile Phe Ile Asp Ser Asp His Thr Asp Asn Gln Arg Ile Leu Glu Phe
            290                 295                 300

Phe Gly Leu Lys Lys Glu Glu Cys Pro Ala Val Arg Leu Ile Thr Leu
305                 310                 315                 320

Glu Glu Glu Met Thr Lys Tyr Lys Pro Glu Ser Glu Glu Leu Thr Ala
                325                 330                 335

Glu Arg Ile Thr Glu Phe Cys His Arg Phe Leu Glu Gly Lys Ile Lys
                340                 345                 350

Pro His Leu Met Ser Gln Glu Arg Ala Asp Gly Asp Trp Asp Lys Gln
            355                 360                 365

Pro Val Lys Val Pro Val Gly Lys Asn Phe Glu Asp Val Ala Phe Asp
            370                 375                 380

Glu Lys Lys Asn Val Phe Val Glu Phe Tyr Ala Pro Trp Cys Gly His
385                 390                 395                 400

Cys Lys Gln Leu Ala Pro Ile Trp Asp Lys Leu Gly Glu Thr Tyr Lys
                405                 410                 415

Asp His Glu Asn Ile Ile Ile Ala Lys Met Asp Ser Thr Ala Asn Glu
            420                 425                 430

Val Glu Ala Val Lys Val His Ser Phe Pro Thr Leu Lys Phe Phe Pro
            435                 440                 445

Ala Ser Ala Asp Arg Thr Val Ile Asp Tyr Asn Gly Glu Arg Thr Leu
450                 455                 460

Asp Gly Phe Lys Lys Phe Leu Glu Ser Gly Gly Gln Asp Gly Ala Gly
465                 470                 475                 480

Asp Asp Asp Asp Leu Glu Asp Leu Glu Glu Ala Glu Glu Pro Asp Met
                485                 490                 495

Glu Glu Asp Asp Asp Gln Lys Ala Val Lys Asp Glu Leu
                500                 505
```

(2) INFORMATION FOR SEQ ID NO:30:

(i) SEQUENCE CHARACTERISTICS:
        (A) LENGTH: 510 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
Met Leu Arg Arg Ala Val Leu Cys Leu Ala Leu Ala Val Thr Ala Gly
1               5                   10                  15

Trp Ala Trp Ala Ala Glu Glu Glu Asp Asn Val Leu Val Leu Lys Ser
                20                  25                  30
```

-continued

```
Ser Asn Phe Ala Glu Glu Leu Ala Ala His Lys Tyr Leu Leu Val Glu
             35                  40                  45

Phe Tyr Ala Pro Trp Cys Gly His Cys Lys Ala Leu Ala Pro Glu Tyr
         50                  55                  60

Ala Lys Ala Ala Gly Lys Leu Lys Ala Glu Gly Ser Asp Ile Arg Leu
 65                  70                  75                  80

Ala Lys Val Asp Ala Thr Glu Glu Ser Asp Leu Ala Gln Gln Tyr Gly
                 85                  90                  95

Val Arg Gly Tyr Pro Thr Ile Lys Phe Phe Lys Asn Gly Asp Thr Ala
                100                 105                 110

Ser Pro Lys Glu Tyr Thr Ala Gly Arg Glu Ala Asp Asp Ile Val Asn
             115                 120                 125

Trp Leu Lys Lys Arg Thr Gly Pro Ala Ala Thr Thr Leu Ala Asp Ser
         130                 135                 140

Ala Ala Ala Glu Ser Leu Val Glu Ser Ser Glu Val Ala Val Ile Gly
145                 150                 155                 160

Phe Phe Lys Asp Val Glu Ser Asp Ala Ala Lys Gln Phe Leu Leu Ala
                165                 170                 175

Ala Glu Ala Thr Asp Asp Ile Pro Phe Gly Leu Thr Ala Ser Ser Asp
            180                 185                 190

Val Phe Ser Arg Tyr Gln Val His Gln Asp Gly Val Val Leu Phe Lys
        195                 200                 205

Lys Phe Asp Glu Gly Arg Asn Asn Phe Glu Gly Glu Val Thr Lys Glu
    210                 215                 220

Lys Leu Leu Asp Phe Ile Lys His Asn Gln Leu Pro Leu Val Ile Glu
225                 230                 235                 240

Phe Thr Glu Gln Thr Ala Pro Lys Ile Phe Gly Gly Glu Ile Lys Thr
                245                 250                 255

His Ile Leu Leu Phe Leu Pro Arg Ser Ala Ala Asp His Asp Gly Lys
            260                 265                 270

Leu Ser Gly Phe Lys Gln Ala Ala Glu Gly Phe Lys Gly Lys Ile Leu
        275                 280                 285

Phe Ile Phe Ile Asp Ser Asp His Ala Asp Asn Gln Arg Ile Leu Glu
    290                 295                 300

Phe Phe Gly Leu Lys Lys Glu Glu Cys Pro Ala Val Arg Leu Ile Thr
305                 310                 315                 320

Leu Glu Glu Glu Met Thr Lys Tyr Lys Pro Glu Ser Asp Glu Leu Thr
                325                 330                 335

Ala Glu Gly Ile Thr Glu Phe Cys Gln Arg Phe Leu Glu Gly Lys Ile
            340                 345                 350

Lys Pro His Leu Met Ser Gln Glu Leu Pro Asp Glu Asp Trp Asp Arg
        355                 360                 365

Gln Pro Val Lys Val Leu Val Gly Lys Asn Phe Glu Glu Val Ala Phe
    370                 375                 380

Asp Glu Lys Lys Asn Val Phe Val Glu Phe Tyr Ala Pro Trp Cys Gly
385                 390                 395                 400

His Cys Lys Gln Leu Ala Pro Ile Trp Asp Lys Leu Gly Glu Thr Tyr
                405                 410                 415

Lys Glu His Gln Asp Ile Val Ile Ala Lys Met Asp Ser Thr Ala Asn
            420                 425                 430

Glu Val Glu Ala Val Lys Val His Ser Phe Pro Thr Leu Lys Phe Phe
        435                 440                 445
```

```
Pro Ala Gly Pro Gly Arg Thr Val Ile Asp Tyr Asn Gly Glu Arg Thr
    450                 455                 460

Leu Asp Gly Phe Lys Lys Phe Leu Glu Ser Gly Gly Gln Asp Gly Ala
465                 470                 475                 480

Gly Asp Glu Asp Gly Leu Glu Asp Leu Glu Glu Ala Glu Glu Pro Asp
                485                 490                 495

Leu Glu Glu Asp Asp Gln Lys Ala Val Arg Asp Glu Leu
            500                 505                 510

(2) INFORMATION FOR SEQ ID NO:31:

(i) SEQUENCE CHARACTERISTICS:
        (A) LENGTH: 493 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

Glu Pro Leu Glu Glu Glu Asp Gly Val Leu Val Leu Arg Ala Ala Asn
1               5                   10                  15

Phe Glu Gln Ala Leu Ala Ala His Arg His Leu Leu Val Glu Phe Tyr
                20                  25                  30

Ala Pro Trp Cys Gly His Cys Lys Ala Leu Ala Pro Glu Tyr Ala Lys
            35                  40                  45

Ala Ala Ala Gln Leu Lys Ala Glu Gly Ser Glu Ile Arg Leu Ala Lys
        50                  55                  60

Val Asp Ala Thr Glu Glu Ala Glu Leu Ala Gln Gln Phe Gly Val Arg
65                  70                  75                  80

Gly Tyr Pro Thr Ile Lys Phe Phe Arg Asn Gly Asp Lys Ala Ala Pro
                85                  90                  95

Arg Glu Tyr Thr Ala Gly Arg Glu Ala Asp Asp Ile Val Ser Trp Leu
            100                 105                 110

Lys Lys Arg Thr Gly Pro Ala Ala Thr Thr Leu Thr Asp Ala Ala Ala
        115                 120                 125

Ala Glu Thr Leu Val Asp Ser Ser Glu Val Val Ile Gly Phe Phe
130                 135                 140

Lys Asp Val Thr Ser Asp Ala Ala Lys Glu Phe Leu Leu Ala Ala Glu
145                 150                 155                 160

Ser Val Asp Asp Ile Pro Phe Gly Ile Ser Ser Ser Ala Asp Val Phe
                165                 170                 175

Ser Lys Tyr Gln Leu Ser Gln Asp Gly Val Val Leu Phe Lys Lys Phe
            180                 185                 190

Asp Glu Gly Arg Asn Asn Phe Glu Gly Asp Leu Thr Lys Asp Asn Leu
        195                 200                 205

Leu Asn Phe Ile Lys Ser Asn Gln Leu Pro Leu Val Ile Glu Phe Thr
210                 215                 220

Glu Gln Thr Ala Pro Lys Ile Phe Gly Gly Glu Ile Lys Thr His Ile
225                 230                 235                 240

Leu Leu Phe Leu Pro Lys Ser Val Ser Asp Tyr Glu Gly Lys Leu Asp
                245                 250                 255

Asn Phe Lys Thr Ala Ala Gly Asn Phe Lys Gly Lys Ile Leu Phe Ile
            260                 265                 270

Phe Ile Asp Ser Asp His Ser Asp Asn Gln Arg Ile Leu Glu Phe Phe
        275                 280                 285
```

```
Gly Leu Lys Lys Glu Cys Pro Ala Val Arg Leu Ile Thr Leu Glu
        290                 295                 300
Glu Glu Met Thr Lys Tyr Lys Pro Glu Ser Asp Asp Leu Thr Ala Asp
305                 310                 315                 320
Lys Ile Lys Glu Phe Cys Asn Lys Phe Leu Glu Gly Lys Ile Lys Pro
                325                 330                 335
His Leu Met Ser Gln Asp Leu Pro Glu Asp Trp Asp Lys Gln Pro Val
            340                 345                 350
Lys Val Leu Val Gly Lys Asn Phe Glu Val Ala Phe Asp Glu Asn
        355                 360                 365
Lys Asn Val Phe Val Glu Phe Tyr Ala Pro Trp Cys Gly His Cys Lys
    370                 375                 380
Gln Leu Ala Pro Ala Trp Asp Lys Leu Gly Pro Thr Tyr Arg Asp His
385                 390                 395                 400
Glu Asn Ile Val Ile Ala Lys Met Asp Ser Thr Ala Asn Glu Val Glu
                405                 410                 415
Ala Val Lys Ile His Ser Phe Pro Thr Leu Lys Phe Phe Pro Ala Gly
            420                 425                 430
Ser Gly Arg Asn Val Ile Asp Tyr Asn Gly Glu Arg Thr Leu Glu Gly
        435                 440                 445
Phe Lys Lys Phe Leu Glu Ser Gly Gly Gln Asp Gly Ala Ala Ala Asp
    450                 455                 460
Asp Asp Leu Glu Asp Leu Glu Thr Asp Glu Thr Asp Leu Glu Glu
465                 470                 475                 480
Gly Asp Asp Asp Glu Gln Lys Ile Gln Lys Asp Glu Leu
            485                 490

(2) INFORMATION FOR SEQ ID NO:32:

(i) SEQUENCE CHARACTERISTICS:
        (A) LENGTH: 521 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

Met Lys Phe Ser Ala Gly Ala Val Leu Ser Trp Ser Leu Leu Leu
1               5                   10                  15
Ala Ser Ser Val Phe Ala Gln Gln Glu Ala Val Ala Pro Glu Asp Ser
                20                  25                  30
Ala Val Val Lys Leu Ala Thr Asp Ser Phe Asn Glu Tyr Ile Gln Ser
            35                  40                  45
His Asp Leu Val Leu Ala Glu Phe Phe Ala Pro Trp Cys Gly His Cys
    50                  55                  60
Lys Asn Met Ala Pro Glu Tyr Val Lys Ala Ala Glu Thr Leu Val Glu
65                  70                  75                  80
Lys Asn Ile Thr Leu Ala Gln Ile Asp Cys Thr Glu Asn Gln Asp Leu
                85                  90                  95
Cys Met Glu His Asn Ile Pro Gly Phe Pro Ser Leu Lys Ile Phe Lys
            100                 105                 110
Asn Ser Asp Val Asn Asn Ser Ile Asp Tyr Glu Gly Pro Arg Thr Ala
        115                 120                 125
Glu Ala Val Gln Phe Met Ile Lys Gln Ser Gln Pro Ala Val Ala Val
    130                 135                 140
```

```
Val Ala Asp Leu Pro Ala Tyr Leu Ala Asn Glu Thr Phe Val Thr Pro
145                 150                 155                 160

Val Ile Val Gln Ser Gly Lys Ile Asp Ala Asp Phe Asn Ala Thr Phe
                165                 170                 175

Tyr Ser Met Ala Asn Lys His Phe Asn Asp Tyr Asp Phe Val Ser Ala
            180                 185                 190

Glu Asn Ala Asp Asp Phe Lys Leu Ser Ile Tyr Leu Pro Ser Ala
        195                 200                 205

Met Asp Glu Pro Val Val Tyr Asn Gly Lys Lys Ala Asp Ile Ala Asp
    210                 215                 220

Ala Asp Val Phe Glu Lys Trp Leu Gln Val Glu Ala Leu Pro Tyr Phe
225                 230                 235                 240

Gly Glu Ile Asp Gly Ser Val Phe Ala Gln Tyr Val Glu Ser Gly Leu
                245                 250                 255

Pro Leu Gly Tyr Leu Phe Tyr Asn Asp Glu Glu Glu Leu Glu Glu Tyr
            260                 265                 270

Lys Pro Leu Phe Thr Glu Leu Ala Lys Lys Asn Arg Gly Leu Met Asn
        275                 280                 285

Phe Val Ser Ile Asp Ala Arg Lys Phe Gly Arg His Ala Gly Asn Leu
290                 295                 300

Asn Met Lys Glu Gln Phe Pro Leu Phe Ala Ile His Asp Met Thr Glu
305                 310                 315                 320

Asp Leu Lys Tyr Gly Leu Pro Gln Leu Ser Glu Glu Ala Phe Asp Glu
                325                 330                 335

Leu Ser Asp Lys Ile Val Leu Glu Ser Lys Ala Ile Glu Ser Leu Asx
            340                 345                 350

Lys Asp Phe Leu Lys Gly Asp Ala Ser Pro Ile Val Lys Ser Gln Glu
        355                 360                 365

Ile Phe Glu Asn Gln Asp Ser Ser Val Phe Gln Leu Val Gly Lys Asn
        370                 375                 380

His Asp Glu Ile Val Asn Asp Pro Lys Lys Asp Val Leu Val Leu Tyr
385                 390                 395                 400

Tyr Ala Pro Trp Cys Gly His Cys Lys Arg Leu Ala Pro Thr Tyr Gln
                405                 410                 415

Glu Leu Ala Asp Thr Tyr Ala Asn Ala Thr Ser Asp Val Leu Ile Ala
            420                 425                 430

Lys Leu Asp His Thr Glu Asn Asp Val Arg Gly Val Val Ile Glu Gly
        435                 440                 445

Tyr Pro Thr Ile Val Leu Tyr Pro Gly Gly Lys Lys Ser Glu Ser Val
    450                 455                 460

Val Tyr Gln Gly Ser Arg Ser Leu Asp Ser Leu Phe Asp Phe Ile Lys
465                 470                 475                 480

Glu Asn Gly His Phe Asp Val Asp Gly Lys Ala Leu Tyr Glu Glu Ala
                485                 490                 495

Gln Glu Lys Ala Ala Glu Glu Ala Asp Ala Asp Ala Glu Leu Ala Asp
            500                 505                 510

Glu Glu Asp Ala Ile His Asp Glu Leu
        515                 520

(2) INFORMATION FOR SEQ ID NO:33:

(i) SEQUENCE CHARACTERISTICS:
        (A) LENGTH: 512 amino acids
        (B) TYPE: amino acid
        (C) STRANDEDNESS: single
```

(D) TOPOLOGY: linear (ii) MOLECULE TYPE: peptide (xi) SEQUENCE DESCRIPTION: SEQ ID NO:33:

```
Met Ala Lys Asn Val Ala Ile Phe Gly Leu Leu Phe Ser Leu Leu Leu
1               5                   10                  15

Leu Val Pro Ser Gln Ile Phe Ala Glu Glu Ser Ser Thr Asp Ala Lys
            20                  25                  30

Glu Phe Val Leu Thr Leu Asp Asn Thr Asn Phe His Asp Thr Val Lys
        35                  40                  45

Lys His Asp Phe Ile Val Val Glu Phe Tyr Ala Pro Trp Cys Gly His
    50                  55                  60

Cys Lys Lys Leu Ala Pro Glu Tyr Glu Lys Ala Ala Ser Ile Leu Ser
65                  70                  75                  80

Thr His Glu Pro Pro Val Val Leu Ala Lys Val Asp Ala Asn Glu Glu
                85                  90                  95

His Asn Lys Asp Leu Ala Ser Glu Asn Asp Val Lys Gly Phe Pro Thr
            100                 105                 110

Ile Lys Ile Phe Arg Asn Gly Gly Lys Asn Ile Gln Glu Tyr Lys Gly
        115                 120                 125

Pro Arg Glu Ala Glu Gly Ile Val Glu Tyr Leu Lys Lys Gln Ser Gly
    130                 135                 140

Pro Ala Ser Thr Glu Ile Lys Ser Ala Asp Asp Ala Thr Ala Phe Val
145                 150                 155                 160

Gly Asp Asn Lys Val Val Ile Gly Val Phe Pro Lys Phe Ser Gly
                165                 170                 175

Glu Glu Tyr Asp Asn Phe Ile Ala Leu Ala Glu Lys Leu Arg Ser Asp
            180                 185                 190

Tyr Asp Phe Ala His Thr Leu Asn Ala Lys His Leu Pro Lys Gly Asp
        195                 200                 205

Ser Ser Val Ser Gly Pro Val Val Arg Leu Phe Lys Pro Phe Asp Glu
    210                 215                 220

Leu Phe Val Asp Ser Lys Asp Phe Asn Val Glu Ala Leu Glu Lys Phe
225                 230                 235                 240

Ile Glu Glu Ser Ser Thr Pro Ile Val Thr Val Phe Asn Asn Glu Pro
                245                 250                 255

Ser Asn His Pro Phe Val Val Lys Phe Phe Asn Ser Pro Asn Ala Lys
            260                 265                 270

Ala Met Leu Phe Ile Asn Phe Thr Thr Glu Gly Ala Glu Ser Phe Lys
        275                 280                 285

Thr Lys Tyr His Glu Val Ala Glu Gln Tyr Lys Gln Gln Gly Val Ser
    290                 295                 300

Phe Leu Val Gly Asp Val Glu Ser Ser Gln Gly Ala Phe Gln Tyr Phe
305                 310                 315                 320

Gly Leu Lys Glu Glu Gln Val Pro Leu Ile Ile Gln His Asn Asp
                325                 330                 335

Gly Lys Lys Phe Phe Lys Pro Asn Leu Glu Leu Asp Gln Leu Pro Thr
            340                 345                 350

Trp Leu Lys Ala Tyr Lys Asp Gly Lys Val Glu Pro Phe Val Lys Ser
        355                 360                 365

Glu Pro Ile Pro Glu Thr Asn Asn Glu Pro Val Lys Val Val Gly
    370                 375                 380

Gln Thr Leu Glu Asp Val Val Phe Lys Ser Gly Lys Asn Val Leu Ile
```

-continued

```
385                 390                 395                 400
Glu Phe Tyr Ala Pro Trp Cys Gly His Cys Lys Gln Leu Ala Pro Ile
                405                 410                 415

Leu Asp Glu Val Ala Val Ser Phe Gln Ser Asp Ala Asp Val Val Ile
                420                 425                 430

Ala Lys Leu Asp Ala Thr Ala Asn Asp Ile Pro Thr Asp Thr Phe Asp
                435                 440                 445

Val Gln Gly Tyr Pro Thr Leu Tyr Phe Arg Ser Ala Ser Gly Lys Leu
                450                 455                 460

Ser Gln Tyr Asp Gly Gly Arg Thr Lys Glu Asp Ile Ile Glu Phe Ile
465                 470                 475                 480

Glu Lys Asn Lys Asp Lys Thr Gly Ala Ala His Gln Glu Val Glu Gln
                485                 490                 495

Pro Lys Ala Ala Ala Gln Pro Glu Ala Glu Gln Pro Lys Asp Glu Leu
                500                 505                 510
```

(2) INFORMATION FOR SEQ ID NO:34:

(i) SEQUENCE CHARACTERISTICS:
        (A) LENGTH: 515 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

```
Met Arg Thr Phe Ala Pro Trp Ile Leu Ser Leu Leu Gly Ala Ser Ala
1               5                   10                  15

Val Ala Ser Ala Ala Asp Ala Thr Ala Glu Ala Pro Ser Asp Val Val
                20                  25                  30

Ser Leu Thr Gly Asp Thr Phe Glu Thr Phe Val Lys Glu His Asp Leu
                35                  40                  45

Val Leu Ala Glu Phe Phe Ala Pro Trp Cys Gly His Cys Lys Ala Leu
                50                  55                  60

Ala Pro Lys Tyr Glu Gln Ala Ala Thr Glu Leu Lys Glu Lys Asn Ile
65                  70                  75                  80

Pro Leu Val Lys Val Asp Cys Thr Glu Glu Ala Leu Cys Arg Asp
                85                  90                  95

Gln Gly Val Glu Gly Tyr Pro Thr Leu Lys Ile Phe Arg Gly Leu Asp
                100                 105                 110

Ala Val Lys Pro Tyr Gln Gly Ala Arg Gln Thr Glu Ala Ile Val Ser
                115                 120                 125

Tyr Met Val Lys Gln Ser Leu Pro Ala Val Ser Pro Val Thr Pro Glu
                130                 135                 140

Asn Leu Glu Glu Ile Lys Thr Met Asp Lys Ile Val Val Ile Gly Tyr
145                 150                 155                 160

Ile Ala Ser Asp Asp Gln Thr Ala Asn Asp Ile Phe Thr Thr Phe Ala
                165                 170                 175

Glu Ser Gln Arg Asp Asn Tyr Leu Phe Ala Ala Thr Ser Asp Ala Ser
                180                 185                 190

Ile Ala Lys Ala Glu Gly Val Lys Gln Pro Ser Ile Val Leu Tyr Lys
                195                 200                 205

Asp Phe Asp Glu Lys Lys Ala Thr Tyr Asp Gly Glu Ile Glu Gln Asp
                210                 215                 220

Ala Leu Leu Ser Trp Val Lys Thr Ala Ser Thr Pro Leu Val Gly Glu
```

-continued

```
                225                 230                 235                 240
Leu Gly Pro Glu Thr Tyr Ser Gly Tyr Ile Thr Ala Gly Ile Pro Leu
                    245                 250                 255

Ala Tyr Ile Phe Ala Glu Thr Lys Glu Arg Glu Gln Phe Thr Glu
                260                 265                 270

Glu Phe Lys Phe Ile Ala Glu Lys His Lys Gly Ser Ile Asn Ile Val
            275                 280                 285

Thr Ile Asp Ala Lys Leu Tyr Gly Ala His Ala Gly Asn Leu Asn Leu
        290                 295                 300

Asp Pro Ser Lys Phe Pro Ala Phe Ala Ile Gln Asp Pro Glu Lys Asn
305                 310                 315                 320

Ala Lys Tyr Pro Tyr Asp Gln Ser Lys Glu Val Lys Ala Lys Asp Ile
                325                 330                 335

Gly Lys Phe Ile Gln Asp Val Leu Asp Asp Lys Val Glu Pro Ser Ile
                340                 345                 350

Lys Ser Glu Ala Ile Pro Glu Thr Gln Glu Gly Pro Val Thr Val Val
            355                 360                 365

Val Ala His Ser Tyr Lys Asp Leu Val Leu Asp Asn Glu Lys Asp Val
        370                 375                 380

Leu Leu Glu Phe Tyr Ala Pro Trp Cys Gly His Cys Lys Ala Leu Ala
385                 390                 395                 400

Pro Lys Tyr Glu Glu Leu Ala Ser Leu Tyr Lys Asp Ile Pro Glu Val
                405                 410                 415

Thr Ile Ala Lys Ile Asp Ala Thr Ala Asn Asp Val Pro Asp Ser Ile
                420                 425                 430

Thr Gly Phe Pro Thr Ile Lys Leu Phe Ala Ala Gly Ala Lys Asp Ser
            435                 440                 445

Pro Val Glu Tyr Glu Gly Ser Arg Thr Val Glu Asp Leu Ala Asn Phe
        450                 455                 460

Val Lys Glu Asn Gly Lys His Lys Val Asp Ala Leu Glu Val Asp Pro
465                 470                 475                 480

Lys Lys Glu Gln Glu Ser Gly Asp Ala Thr Glu Thr Arg Ala Ala Ser
                485                 490                 495

Asp Glu Thr Glu Thr Pro Ala Ala Thr Ser Asp Asp Lys Ser Glu His
            500                 505                 510

Asp Glu Leu
        515

(2) INFORMATION FOR SEQ ID NO:35:

(i) SEQUENCE CHARACTERISTICS:
        (A) LENGTH: 530 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

Met Lys Phe Ser Ala Gly Ala Val Leu Ser Trp Ser Ser Leu Leu Leu
1               5                   10                  15

Ala Ser Ser Val Phe Ala Gln Gln Glu Ala Val Ala Pro Glu Asp Ser
                20                  25                  30

Ala Val Val Lys Leu Ala Thr Asp Ser Phe Asn Glu Tyr Ile Gln Ser
            35                  40                  45

His Asp Leu Val Leu Ala Glu Phe Phe Ala Pro Trp Cys Gly His Cys
```

-continued

```
              50                  55                  60
Lys Asn Met Ala Pro Glu Tyr Val Lys Ala Ala Glu Thr Leu Val Glu
 65                  70                  75                  80

Lys Asn Ile Thr Leu Ala Gln Ile Asp Cys Thr Glu Asn Gln Asp Leu
                 85                  90                  95

Cys Met Glu His Asn Ile Pro Gly Phe Pro Ser Leu Lys Ile Phe Lys
                100                 105                 110

Asn Arg Asp Val Asn Ser Ile Asp Tyr Glu Gly Pro Arg Thr Ala
            115                 120                 125

Glu Ala Ile Val Gln Phe Met Ile Lys Gln Ser Gln Pro Ala Val Ala
            130                 135                 140

Val Val Ala Asp Leu Pro Ala Tyr Leu Ala Asn Glu Thr Phe Val Thr
145                 150                 155                 160

Pro Val Ile Val Gln Ser Gly Lys Ile Asp Ala Asp Phe Asn Ala Thr
                165                 170                 175

Phe Tyr Ser Met Ala Asn Lys His Phe Asn Asp Tyr Asp Phe Val Ser
                180                 185                 190

Ala Glu Asn Ala Asp Asp Phe Lys Leu Ser Ile Tyr Leu Pro Ser
            195                 200                 205

Ala Met Asp Glu Pro Val Val Tyr Asn Gly Lys Lys Ala Asp Ile Ala
            210                 215                 220

Asp Ala Asp Val Phe Glu Lys Trp Leu Gln Val Glu Ala Leu Pro Tyr
225                 230                 235                 240

Phe Gly Glu Ile Asp Gly Ser Val Phe Ala Gln Tyr Val Glu Ser Gly
                245                 250                 255

Leu Pro Leu Gly Tyr Leu Phe Tyr Asn Asp Glu Glu Leu Glu Glu
            260                 265                 270

Tyr Lys Pro Leu Phe Thr Glu Leu Ala Lys Lys Asn Arg Gly Leu Met
            275                 280                 285

Asn Phe Val Ser Ile Asp Ala Arg Lys Phe Gly Arg His Ala Gly Asn
            290                 295                 300

Leu Asn Met Lys Glu Gln Phe Pro Leu Phe Ala Ile His Asp Met Thr
305                 310                 315                 320

Glu Asp Leu Lys Tyr Gly Leu Pro Gln Leu Ser Glu Glu Ala Phe Asp
                325                 330                 335

Glu Leu Ser Asp Lys Ile Val Leu Glu Ser Lys Ala Ile Glu Ser Leu
            340                 345                 350

Val Lys Asp Phe Leu Lys Gly Asp Ala Ser Pro Ile Val Lys Ser Gln
            355                 360                 365

Glu Ile Phe Glu Asn Gln Asp Ser Ser Val Phe Gln Leu Val Gly Lys
            370                 375                 380

Asn His Asp Glu Ile Val Asn Asp Pro Lys Lys Asp Val Leu Val Leu
385                 390                 395                 400

Tyr Tyr Ala Pro Trp Cys Gly His Cys Lys Arg Leu Ala Pro Thr Tyr
                405                 410                 415

Gln Glu Leu Ala Asp Thr Tyr Ala Asn Ala Thr Ser Asp Val Leu Ile
            420                 425                 430

Ala Lys Leu Asp His Thr Glu Asn Asp Val Arg Gly Val Val Ile Glu
            435                 440                 445

Gly Tyr Pro Thr Ile Val Leu Tyr Pro Gly Gly Lys Lys Ser Glu Ser
            450                 455                 460

Val Val Tyr Gln Gly Ser Arg Ser Leu Asp Ser Leu Phe Asp Phe Ile
465                 470                 475                 480
```

```
Lys Glu Asn Gly His Phe Asp Val Asp Gly Lys Ala Leu Tyr Glu Glu
                485                 490                 495

Ala Gln Glu Lys Ala Ala Glu Glu Ala Glu Ala Asp Ala Glu Ala Glu
            500                 505                 510

Ala Asp Ala Asp Ala Glu Leu Ala Asp Glu Glu Asp Ala Ile His Asp
        515                 520                 525

Glu Leu
    530

(2) INFORMATION FOR SEQ ID NO:36:

(i) SEQUENCE CHARACTERISTICS:
        (A) LENGTH: 510 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

Met Leu Arg Arg Ala Leu Leu Cys Leu Ala Leu Thr Ala Leu Phe Arg
1               5                   10                  15

Ala Gly Ala Gly Ala Pro Asp Glu Glu Asp His Val Leu Val Leu His
            20                  25                  30

Lys Gly Asn Phe Asp Glu Ala Leu Ala Ala His Lys Tyr Leu Leu Val
            35                  40                  45

Glu Phe Tyr Ala Pro Trp Cys Gly His Cys Lys Ala Leu Ala Pro Glu
    50                  55                  60

Tyr Ala Lys Ala Ala Gly Lys Leu Lys Ala Glu Gly Ser Glu Ile Arg
65                  70                  75                  80

Leu Ala Lys Val Asp Ala Thr Glu Glu Ser Asp Leu Ala Gln Gln Tyr
                85                  90                  95

Gly Val Arg Gly Tyr Pro Thr Ile Lys Phe Phe Lys Asn Gly Asp Thr
            100                 105                 110

Ala Ser Pro Lys Glu Tyr Thr Ala Gly Arg Glu Ala Asp Asp Ile Val
            115                 120                 125

Asn Trp Leu Lys Lys Arg Thr Gly Pro Ala Ala Ser Thr Leu Ser Asp
130                 135                 140

Gly Ala Ala Glu Ala Leu Val Glu Ser Ser Glu Val Ala Val Ile
145                 150                 155                 160

Gly Phe Phe Lys Asp Met Glu Ser Asp Ser Ala Lys Gln Phe Phe Leu
                165                 170                 175

Ala Ala Glu Val Ile Asp Asp Ile Pro Phe Gly Ile Thr Ser Asn Ser
            180                 185                 190

Asp Val Phe Ser Lys Tyr Gln Leu Asp Lys Asp Gly Val Val Leu Phe
            195                 200                 205

Lys Lys Phe Asp Glu Gly Arg Asn Asn Phe Glu Gly Glu Val Thr Lys
        210                 215                 220

Glu Lys Leu Leu Asp Phe Ile Lys His Asn Gln Leu Pro Leu Val Ile
225                 230                 235                 240

Glu Phe Thr Glu Gln Thr Ala Pro Lys Ile Phe Gly Gly Glu Ile Lys
                245                 250                 255

Thr His Ile Leu Leu Phe Leu Pro Lys Ser Val Ser Asp Tyr Glu Gly
            260                 265                 270

Lys Leu Ser Asn Phe Lys Lys Ala Glu Ser Phe Lys Gly Lys Ile
            275                 280                 285
```

```
Leu Phe Ile Phe Ile Asp Ser Asp His Thr Asp Asn Gln Arg Ile Leu
    290                 295                 300
Glu Phe Glu Gly Leu Lys Lys Glu Cys Pro Ala Val Arg Leu Ile
305                 310                 315                 320
Thr Leu Glu Glu Glu Met Thr Lys Tyr Lys Pro Glu Ser Asp Glu Leu
                    325                 330                 335
Thr Ala Glu Lys Ile Thr Glu Phe Cys His Arg Phe Leu Glu Gly Lys
                340                 345                 350
Ile Lys Pro His Leu Met Ser Gln Glu Leu Pro Asp Asp Trp Asp Lys
            355                 360                 365
Gln Pro Val Lys Val Leu Val Gly Lys Asn Phe Glu Glu Val Ala Phe
    370                 375                 380
Asp Glu Lys Lys Asn Val Phe Val Glu Phe Tyr Ala Pro Trp Cys Gly
385                 390                 395                 400
His Cys Lys Gln Leu Ala Pro Ile Trp Asp Lys Leu Gly Glu Thr Tyr
                405                 410                 415
Lys Asp His Glu Asn Ile Val Ile Ala Lys Met Asp Ser Thr Ala Asn
                420                 425                 430
Glu Val Glu Ala Val Lys Val His Ser Phe Pro Thr Leu Lys Phe Phe
            435                 440                 445
Pro Ala Ser Ala Asp Arg Thr Val Ile Asp Tyr Asn Gly Glu Arg Thr
    450                 455                 460
Leu Asp Gly Phe Lys Lys Phe Leu Glu Ser Gly Gly Gln Asp Gly Ala
465                 470                 475                 480
Gly Asp Asp Asp Asp Leu Glu Asp Leu Glu Glu Ala Glu Glu Pro Asp
                485                 490                 495
Leu Glu Glu Asp Asp Asp Gln Lys Ala Val Lys Asp Glu Leu
                500                 505                 510

(2) INFORMATION FOR SEQ ID NO:37:

(i) SEQUENCE CHARACTERISTICS:
        (A) LENGTH: 508 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

Met Leu Ser Arg Ala Leu Leu Cys Leu Ala Leu Ala Trp Ala Ala Arg
1               5                   10                  15
Val Gly Ala Asp Ala Leu Glu Glu Glu Asp Asn Val Leu Val Leu Lys
                20                  25                  30
Lys Ser Asn Phe Ala Glu Pro Ala Ala His Asn Tyr Leu Leu Val Glu
            35                  40                  45
Phe Tyr Ala Pro Trp Cys Gly His Cys Lys Ala Leu Ala Pro Glu Tyr
    50                  55                  60
Ala Lys Ala Ala Ala Lys Leu Lys Ala Glu Gly Ser Glu Ile Arg Leu
65                  70                  75                  80
Ala Lys Val Asp Ala Thr Glu Glu Ser Asp Leu Ala Gln Gln Tyr Gly
                85                  90                  95
Val Arg Gly Tyr Pro Thr Ile Lys Phe Phe Lys Asn Gly Asp Thr Ala
                100                 105                 110
Ser Pro Lys Glu Tyr Thr Ala Gly Arg Glu Ala Asp Asp Ile Val Asn
            115                 120                 125
```

```
Trp Leu Lys Lys Arg Thr Gly Pro Ala Ala Thr Thr Leu Ser Asp Thr
    130                 135                 140

Ala Ala Ala Glu Ser Leu Val Asp Ser Ser Glu Val Thr Val Ile Gly
145                 150                 155                 160

Phe Phe Lys Asp Ala Gly Ser Asp Ser Ala Lys Gln Phe Leu Leu Ala
                165                 170                 175

Ala Glu Ala Val Asp Asp Ile Pro Phe Gly Ile Thr Ser Asn Ser Asp
                180                 185                 190

Val Phe Ser Lys Tyr Gln Leu Asp Lys Asp Gly Val Val Leu Phe Lys
                195                 200                 205

Lys Phe Asp Glu Gly Arg Asn Asn Phe Glu Gly Glu Ile Thr Lys Glu
    210                 215                 220

Lys Leu Leu Asp Phe Ile Lys His Asn Gln Leu Pro Leu Val Ile Glu
225                 230                 235                 240

Phe Thr Glu Gln Thr Ala Pro Lys Ile Phe Gly Gly Glu Ile Lys Thr
                245                 250                 255

His Ile Leu Leu Phe Leu Pro Lys Ser Val Ser Asp Tyr Asp Gly Lys
                260                 265                 270

Leu Ser Asn Phe Lys Lys Ala Ala Glu Gly Phe Lys Gly Lys Ile Leu
    275                 280                 285

Phe Ile Phe Ile Asp Ser Asp His Thr Asp Asn Gln Arg Ile Leu Glu
290                 295                 300

Phe Phe Gly Leu Lys Lys Glu Glu Cys Pro Ala Val Arg Leu Ile Thr
305                 310                 315                 320

Leu Glu Glu Glu Met Thr Lys Tyr Lys Pro Glu Ser Asp Glu Leu Thr
                325                 330                 335

Ala Glu Lys Ile Thr Gln Phe Cys His His Phe Leu Glu Gly Lys Ile
                340                 345                 350

Lys Pro His Leu Met Ser Gln Glu Leu Pro Glu Asp Trp Asp Lys Gln
    355                 360                 365

Pro Val Lys Val Leu Val Gly Lys Asn Phe Glu Glu Val Ala Phe Asp
370                 375                 380

Glu Lys Lys Asn Val Phe Val Glu Phe Tyr Ala Pro Trp Cys Gly His
385                 390                 395                 400

Cys Lys Gln Leu Ala Pro Ile Trp Asp Lys Leu Gly Glu Thr Tyr Lys
                405                 410                 415

Asp His Glu Asn Ile Val Ile Ala Lys Met Asp Ser Thr Ala Asn Glu
                420                 425                 430

Val Glu Ala Val Lys Val His Ser Phe Pro Thr Leu Lys Phe Phe Pro
    435                 440                 445

Ala Ser Ala Asp Arg Thr Val Ile Asp Tyr Asn Gly Glu Arg Thr Leu
450                 455                 460

Asp Gly Phe Lys Lys Phe Leu Glu Ser Gly Arg Gln Asp Gly Ala Gly
465                 470                 475                 480

Asp Asn Asp Asp Leu Asp Leu Glu Glu Ala Leu Glu Pro Asp Met Glu
                485                 490                 495

Glu Asp Asp Asp Gln Lys Ala Val Lys Asp Glu Leu
                500                 505
```

(2) INFORMATION FOR SEQ ID NO:38:

(i) SEQUENCE CHARACTERISTICS:
        (A) LENGTH: 638 amino acids
        (B) TYPE: amino acid

```
           (C) STRANDEDNESS: single
           (D) TOPOLOGY: linear (ii) MOLECULE TYPE: peptide (xi) SEQUENCE DESCRIPTION: SEQ ID NO:38:

Met Lys Leu Arg Lys Ala Trp Leu Leu Val Leu Leu Ala Leu Thr
1               5                   10                  15

Gln Leu Leu Ala Ala Ala Ser Ala Gly Asp Ala Gln Glu Asp Thr Ser
            20                  25                  30

Asp Thr Glu Asn Ala Thr Glu Glu Glu Glu Glu Asp Asp Asp Asp
            35                  40                  45

Leu Glu Val Lys Glu Glu Asn Gly Val Trp Val Leu Asn Asp Gly Asn
    50                  55                  60

Phe Asp Asn Phe Val Ala Asp Lys Asp Thr Val Leu Leu Glu Phe Tyr
65                  70                  75                  80

Ala Pro Trp Cys Gly His Cys Lys Gln Phe Ala Pro Glu Tyr Glu Lys
                85                  90                  95

Ile Ala Ser Thr Leu Lys Asp Asn Asp Pro Pro Ile Ala Val Ala Lys
                100                 105                 110

Ile Asp Ala Thr Ser Ala Ser Met Leu Ala Ser Lys Phe Asp Val Ser
                115                 120                 125

Gly Tyr Pro Thr Ile Lys Ile Leu Lys Lys Gly Gln Ala Val Asp Tyr
    130                 135                 140

Asp Gly Ser Arg Thr Gln Glu Glu Ile Val Ala Lys Val Arg Glu Val
145                 150                 155                 160

Ser Gln Pro Asp Trp Thr Pro Pro Glu Val Thr Leu Ser Leu Thr
                165                 170                 175

Lys Asp Asn Phe Asp Asp Val Val Asn Asn Ala Asp Ile Ile Leu Val
                180                 185                 190

Glu Phe Tyr Ala Pro Trp Cys Gly His Cys Lys Lys Leu Ala Pro Glu
            195                 200                 205

Tyr Glu Lys Ala Ala Lys Glu Leu Ser Lys Arg Ser Pro Pro Ile Pro
210                 215                 220

Leu Ala Lys Val Asp Ala Thr Glu Gln Thr Asp Leu Ala Lys Arg Phe
225                 230                 235                 240

Asp Val Ser Gly Tyr Pro Thr Leu Lys Ile Phe Arg Lys Gly Arg Pro
                245                 250                 255

Phe Asp Tyr Asn Gly Pro Arg Glu Lys Tyr Gly Ile Val Asp Tyr Met
            260                 265                 270

Ile Glu Gln Ser Gly Pro Pro Ser Lys Glu Ile Leu Thr Leu Lys Gln
            275                 280                 285

Val Gln Glu Phe Leu Lys Asp Gly Asp Val Val Ile Ile Gly Leu
    290                 295                 300

Phe Gln Gly Asp Gly Asp Pro Ala Tyr Leu Gln Tyr Gln Asp Ala Ala
305                 310                 315                 320

Asn Asn Leu Arg Glu Asp Tyr Lys Phe His His Thr Phe Ser Pro Glu
                325                 330                 335

Ile Ala Lys Phe Leu Lys Val Ser Leu Gly Lys Leu Val Leu Thr His
                340                 345                 350

Pro Glu Lys Phe Gln Ser Lys Tyr Glu Pro Arg Phe His Val Met Asp
                355                 360                 365

Val Gln Gly Ser Thr Glu Ala Ser Ala Ile Lys Asp Tyr Val Val Lys
    370                 375                 380
```

```
His Ala Leu Pro Leu Val Gly His Arg Lys Thr Ser Asn Asp Ala Lys
385                 390                 395                 400

Arg Tyr Ser Lys Arg Pro Leu Val Val Tyr Tyr Ser Val Asp Phe
            405                 410                 415

Ser Phe Asp Tyr Arg Ala Ala Thr Gln Phe Trp Arg Asn Lys Val Leu
            420                 425                 430

Glu Val Ala Lys Asp Phe Pro Glu Tyr Thr Phe Ala Ile Ala Asp Glu
        435                 440                 445

Glu Asp Tyr Ala Thr Glu Val Lys Asp Leu Gly Leu Ser Glu Ser Gly
    450                 455                 460

Glu Asp Val Asn Ala Ala Ile Leu Asp Glu Ser Gly Lys Lys Phe Ala
465                 470                 475                 480

Met Glu Pro Glu Glu Phe Asp Ser Asp Thr Leu Arg Glu Phe Val Thr
                485                 490                 495

Ala Phe Lys Lys Gly Lys Leu Lys Pro Val Ile Lys Ser Gln Pro Val
            500                 505                 510

Pro Lys Asn Asn Lys Gly Pro Val Lys Val Val Val Gly Lys Thr Phe
            515                 520                 525

Asp Ala Ile Val Met Asp Pro Lys Lys Asp Val Leu Ile Glu Phe Tyr
    530                 535                 540

Ala Pro Trp Cys Gly His Cys Lys Gln Leu Glu Pro Ile Tyr Thr Ser
545                 550                 555                 560

Leu Gly Lys Lys Tyr Lys Gly Gln Lys Asp Leu Val Ile Ala Lys Met
            565                 570                 575

Asp Ala Thr Ala Asn Asp Ile Thr Asn Asp Gln Tyr Lys Val Glu Gly
            580                 585                 590

Phe Pro Thr Ile Tyr Phe Ala Pro Ser Gly Asp Lys Lys Asn Pro Ile
        595                 600                 605

Lys Phe Glu Gly Gly Asn Arg Asp Leu Glu His Leu Ser Lys Phe Ile
        610                 615                 620

Asp Glu His Ala Thr Lys Arg Ser Arg Thr Lys Glu Glu Leu
625                 630                 635
```

FUNGAL PROTEIN DISULFIDE ISOMERASE

CROSS-REFERENCE TO RELATED APPLICATIONS

Figure 1:
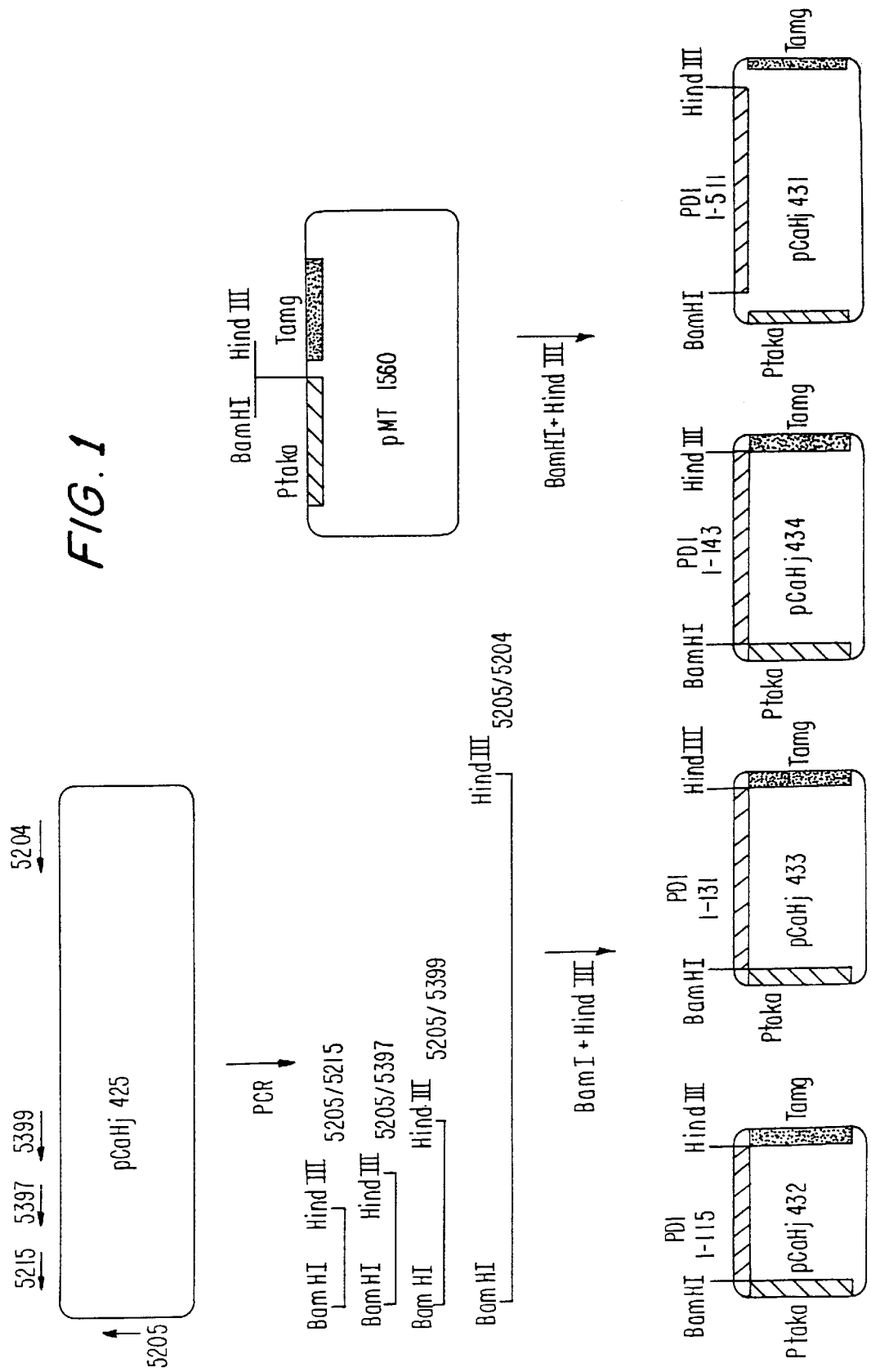

This application is a divisional of U.S. Ser. No. 08/557,122 filed Dec. 11, 1995, now U.S. Pat. No. 5,879,664 which is a 35 U.S.C. 371 national application of PCT/DK94/00266 filed Jun. 28, 1994 and claims priority under 35 U.S.C. 119 of Danish application 0768/93 filed Jun. 28, 1993, the contents of which are fully incorporated herein by reference.

FIELD OF THE INVENTION

The present invention relates to an active recombinant fungal protein disulfide isomerase, compositions comprising said fungal protein disulfide isomerase, and methods for their use; a DNA construct comprising a DNA sequence encoding said fungal protein disulfide isomerase, and a vector and cell harbouring the DNA construct. Furthermore, the present invention relates to a method of preparing the fungal protein disulfide isomerase by use of both traditional and recombinant DNA techniques.

BACKGROUND OF THE INVENTION

The use of protein disulfide redox agents such as protein disulfide isomerases (PDI), and thioredoxins (TRX) for various purposes has been known for some time.

Protein disulfide redox agents catalyse the general reaction:

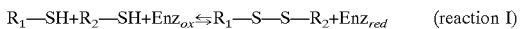

$$R_1\text{—SH} + R_2\text{—SH} + \text{Enz}_{ox} \leftrightarrows R_1\text{—S—S—}R_2 + \text{Enz}_{red} \quad \text{(reaction I)}$$

where $R_1$ and $R_2$ represent protein entities which are the same or different, either within the same polypeptide or in two polypeptides, $\text{Enz}_{ox}$ is a protein disulfide redox agent in the oxidised state, and $\text{Enz}_{red}$ is a protein disulfide redox agent in the reduced state. EC 5.3.4.1 refers to an enzyme capable of capable of catalysing the rearrangement of —S—S— bonds in proteins and EC 1.6.4.4 and EC 1.8.4.2 is an example of enzymes catalysing the reaction with NAD(P)H and glutathione as a mediator, respectively.

This type of activity has been designated as protein disulfide isomerase, sulfhydryl oxidase, protein disulfide reductase, disulfide isomerase, protein disulfide transhydrogenase, and sulfhydryl oxidase.

Disulfide linkages in proteins are formed between cysteine residues and have the general function of stabilising the three dimensional structure of the proteins. They can be formed between cysteine residues of the same or different polypeptides.

Disulfide linkages are present in many types of proteins such as enzymes, structural proteins, etc. Enzymes are catalytic proteins such as proteases, amylases, etc., while structural proteins can be scleroproteins such as keratin, etc. Protein material in hair, wool, skin, leather, hides, food, fodder, stains, and human tissue contains disulfide linkages. Treatment of some of these materials with PDI and TRX, and a redox partner have been described previously.

The use of TRX for waving, straightening, removing and softening of human and animal hair was described by Pigiet et al. (EP 183506 and WO 8906122). Pigiet (U.S. Pat. No. 4,771,036) also describes the use of TRX for prevention and reversal of cataracts. Schreiber (DE 2141763 and DE 2141764) describes the use of protein disulfide transhydrogenase for changing the form of human hair. Pigiet (EP 225156) describes the use of TRX for refolding denatured proteins. Use of TRX to prevent metal catalysed oxidative damage in biological reactions is described by Pigiet et al. (EP 237189).

Toyoshima et al. (EP 277563 and EP 293793) describes the use of PDI to catalyse renaturation of proteins having reduced disulfide linkages or unnatural oxidised disulfide linkages, in particular in connection with renaturation of recombinantly produced proteins. Brockway (EP 272781), and King and Brockway (EP 276547) describe the use of PDI for reconfiguration of human hair, and for treatment of wool, respectively. Sulfhydryl oxidase for the treatment of Ultra-high temperature sterilized milk is described in U.S. Pat. Nos. 4,894,340, 4,632,905, 4,081,328 and 4,053,644. Schreiber (DE 2141763 and DE 2141764) describes the use of protein disulfide transhydrogenase for changing the form of human hair.

The uses of such enzymes have all been connected with reduction of protein disulfide linkages to free protein sulhydryl groups and/or the oxidation of protein sylfhydryl groups to protein disulfide linkages, and/or the rearrangement of disulfide linkages in the same or between different polypeptides, and sometimes to the use of these processes in sequence.

Protein disulfide redox agents can be divided into two main groups of enzymes, thioredoxin type (TRX), and protein disulfide isomerase type (PDI).

Both these can be modified to obtain protein engineered derivatives, chemical modifications and hybrids of TRX and/or PDI (ENG).

TRX is a 12-kDa protein having a redox-active disulfide/dithiol and catalysing thiol-disulfide exchange reactions (Edman et al., Nature 317:267–270, 1985; Holmgren, Ann. Rev. Biochem. 54:237–271, 1985; Holmgren, J. Biol. Chem. 264:13963–13966, 1989). PDI consists of two subunits, each consisting of two domains which are homologous to TRX.

TRX and PDI can be obtained from a number of sources: PDI: protein disulfide isomerases have mainly been identified from mammalian sources, such as Bovine (Yamauchi et al., Biochem. Biophys. Res. Commun. 146:1485–1492, 1987), Chicken (Parkkonen et al., Biochem. J. 256:1005–1011, 1988), Human (Rapilajaniemi et al. EMBO J. 6:643–649, 1987), Mouse (Gong, et al., Nucleic Acids Res. 16:1203, 1988), Rabbit (Fliegel et al., J. Biol. Chem. 265:15496–15502, 1990), and Rat (Edman et al., Nature 317:267–270, 1985). PDI has furthermore been isolated from yeast (Tachikawa et al., J. Biochem. 110:306–313).

TRX: Thioredoxin has been identified from bacteriophages, bacteria such as *Escherichia coli* (Wallace and Kusher, Gene 32:399–408, 1984) and *Bacillus subtilis* (Chen et al. J. Biol Chem. 262:8787–8798, 1987) and eukaryotes.

It would be desirable to facilitate the production of protein disulfide isomerase (PDI), to be able of producing both larger amounts of the enzyme and to produce it in a more economical manner than what is possible by the prior art methods.

Engineered variants (ENG) with improved properties for particular applications are also highly desirable and can be prepared by a variety of methods based on standard recombinant DNA technology:

1) by using site-directed or random mutagenesis to modify the genes encoding TRX or PDI in order to obtain ENG with one or few amino acid changes, 2) by inhibiting or otherwise avoiding dimerisation of the subunits of PDI, thus giving rise to PDI monomers, 3) by producing partial monomers of PDI or TRX, in which regions of the NH2- or COOH termini of PDI or TRX are lacking, 4) by creating hybrids of PDI, TRX and/or ENG, 5) by chemically or enzymatically modifying the products of 1)–4), 6) by a combination of any of 1)–5).

ENG produced according to 1) were described by Lundström et al. (J. Biol. Chem. 267:9047–9052, 1992) and by a combination of 3) and 5) by Pigiet (WO 8906122).

PDI, and TRX can, apart from their natural sources, be obtained by expression of recombinant DNA encoding plant, animal, human or microbial PDI, or TRX, in various hosts, such as microorganisms followed by purification of PDI, or TRX from extracts or supernatants of said host organisms. This goes also for ENG. Preparation of Trx from natural sources is described by Luthman and Holmgren (Biochem. 121:6628–6633, 1982), Wada and Buchanan (in "Thioredoxins, structure and function" (Gadal, Ed.) Editions du Centre National de la Recherche Scientifique), Porque et al. (J. Biol. Chem. 245:2362–2379, 1970) and by Laurent et al. (J. Biol. Chem. 239:3436–3445), whereas recombinant production of TRX is described by Krause et al. (J. Biol. Chem. 266:9494–9500). PDI or sulfhydryl oxidase has been prepared from natural sources by Lambert and Freedman (Biochem J. 213:225–234, 1983), Starnes et al. (U.S. Pat. No. 4,632,905) and Hammer et al. (U.S. Pat. No. 4,894,340), and by recombinant technology by among others Yamauchi et al. (Biochem. Biophys. Res. Commun. 146:1485–1492, 1987). Finally, recombinant production of an ENG is described by Lundström et al. (J. Biol. Chem. 267:9047–9052, 1992).

SUMMARY OF THE INVENTION

The present inventors have succeeded in cloning a DNA sequence encoding a fungal protein disulfide isomerase from filamentous fungi and in obtaining expression of an active protein disulfide isomerase from said DNA sequence, both in the same species and in other organisms, especially microorganisms, and preferably in fungi.

Accordingly, in a first aspect the present invention relates to an active protein disulfide isomerase obtainable from filamentous fungi, specifically fungi belonging to the genus Aspergillus, and especially a protein disulfide isomerase obtainable from *A. oryzae*, or *A. niger*, which enzyme is immunologically reactive with an antibody raised against a purified protein disulfide isomerase derived from *Aspergillus oryzae*, IFO 4177, or *Aspergillus niger*, A524.

From the sequence of the isolated enzyme it can be seen that the protein disulfide isomerase has two -Cys-X-Y-Cys- subunits in positions 58–61 and 393–396. The invention consequently also comprises active truncated forms of the enzymes of the invention, wherein at least one subunit is retained. Examples hereof could be an enzyme having an amino acid sequence corresponding to the residues 20 to 100, residues 330 to 450, or residues 360 to 430 of the appended SEQ ID No. 3, or the corresponding sequence of the enzyme of the invention in question.

Under this aspect, the invention specifically relates to enzymes exhibiting protein disulfide isomerase activity comprising the amino acid residues 1–131, 1–141, 1–143, 1–163, 1–174, or 1–281, of the amino acid sequence shown in the appended SEQ ID No. 3, or variants thereof exhibiting a protein disulfide isomerase activity. Further specific enzymes are enzymes exhibiting protein disulfide isomerase activity comprising the amino acid residues 1–115, of the amino acid sequence shown in the appended SEQ ID No. 3 extended with the following sequence: Leu-Ile-Arg-Glu-Leu-Leu-Gln-Glu-Leu-Val-Asn-Lys-His-Leq (SEQ ID NO. 11); and an enzyme comprising the amino acid residues 1–511, of the amino acid sequence shown in the appended SEQ ID No. 3, and wherein the amino acid residue in position 511 is changed from Glu to Ala.

In the present context, the term "derived from" is intended not only to indicate a protein disulfide isomerase produced by strains IFO 4177 or A524, but also a protein disulfide isomerase encoded by a DNA sequence isolated from these strains such as indicated in SEQ ID No. 1 and SEQ ID No. 2, or a sequence homologous thereto encoding a polypeptide with protein disulfide isomerase activity and produced in a host organism transformed with said DNA sequence.

Accordingly, the present invention thus relates to an enzyme exhibiting protein disulfide isomerase activity, which enzyme is immunologically reactive with an antibody raised against a purified protein disulfide isomerase derived from *Aspergillus oryzae*, IFO 4177.

In the present context, the term "homologue" is intended to indicate a polypeptide encoded by DNA which hybridizes to the same probe as the DNA coding for the protein disulfide isomerase enzyme under certain specified conditions (such as presoaking in 5×SSC and prehybridizing for 1 h at ~40° C. in a solution of 5×SSC, 5×Denhardt's solution, 50 mM sodium phosphate, pH 6.8, and 50 µg of denatured sonicated calf thymus DNA, followed by hybridization in the same solution supplemented with 50 µCi 32-P-dCTP labelled probe for 18 h at ~40° C. followed by washing three times in 2×SSC, 0.2% SDS at 40° C. for 30 minutes). More specifically, the term is intended to refer to a DNA sequence which is at least 70% homologous to the sequences indicated above encoding the protein disulfide isomerase of the invention. The term is intended to include modifications of the DNA sequences indicated above, such as nucleotide substitutions which do not give rise to another amino acid sequence of the protein disulfide isomerase but which correspond to the codon usage of the host organism into which the DNA construct is introduced or nucleotide substitutions which do give rise to a different amino acid sequence and therefore, possibly, a different protein structure which might give rise to a protein disulfide isomerase mutant with different properties than the native enzyme. Other examples of possible modifications are insertion of one or more nucleotides into the sequence, addition of one or more nucleotides at either end of the sequence, or deletion of one or more nucleotides at either end or within the sequence.

In the present context the term active protein disulfide isomerase is intended to indicate an enzyme having an activity similar to that of protein disulfide isomerase, i.e. an enzyme capable of catalysing reaction I. The activity may be determined in an assay based on oxidative refolding of reduced Bowman-Birk soya bean inhibitor, e.g. as described in the Materials and Methods section below.

The term "recombinant" as used about the protein disulfide isomerase of the invention is intended to indicate that it is produced by a cell transformed with a DNA sequence encoding the protein disulfide isomerase. Thus, the recombinant protein disulfide isomerase may be produced by either its parent organism or another organism.

In a further aspect the present invention relates to a DNA construct comprising a DNA sequence encoding an active recombinant protein disulfide isomerase of the invention as defined above. Such a DNA construct may comprise introns (an example thereof is shown in the appended SEQ ID No. 1) and/or regulatory elements native to the parts coding for the mature protein disulfide isomerase of the invention, or be a cDNA construct comprising only that part coding for the mature protein disulfide isomerase (an example being the appended SEQ ID No.2).

In still further aspects the present invention relates to a recombinant expression vector harbouring the DNA construct of the invention, to a cell which either harbours the DNA construct or the expression vector of the invention, and to a process for the production of a protein disulfide isomerase of the invention, wherein a cell of the invention as described above is cultured under conditions conducive to the production of the protein disulfide isomerase, and the protein disulfide isomerase is subsequently recovered from the culture.

Finally, the present invention relates to compositions comprising the active protein disulfide isomerase of the invention and methods for their use in various applications.

BRIEF DESCRIPTION OF THE TABLES AND DRAWING

The invention is further illustrated in the accompanying tables and drawing, in which Table 1 shows an alignment of published eukaryotic PDI amino acid sequences: Bovine (*Bos taurus*) (Yamauchi et al., Biochem. Biophys. Res. Commun. 146:1485–1492, 1987), chicken (*Gallus gallus*) (Parkkonen et al., Biochem. J. 256:1005–1011, 1988), human (*Homo sapiens*) (Rapilajaniemi et al. EMBO J. 6:643–649, 1987), mouse (*Mus musculus*) (Gong, et al., Nucleic Acids Res. 16:1203, 1988), rabbit (*Oryctolagus cuniculus*) (Fliegel et al., J. Biol. Chem. 265:15496–15502, 1990), rat (*Rattus norvegicus*) (Edman et al., Nature 317:267–270, 1985), and yeast (*Sacchaaromyces cerevisiae*) (Tachikawa et al., J. Biochem. 110:306–313).

Table 2 shows an alignment of PDI amino acid sequences: Alfalfa (*Medicago sativa*) (Shorrosh and Dixon, Plant. Mol. Bio. 19:319–321, 1992), *A. oryzae* (this invention), yeast (*Saccharomyces cerevisiae*) (Tachikawa et al., J. Biochem. 110:306–313), bovine (*Bos taurus*) (Yamauchi et al., Biochem. Biophys. Res. Commun. 146:1485–1492, 1987), rat (*Rattus norvegicus*) (Edman et al., Nature 317:267–270, 1985), and mouse (*Mus musculus*) (Gong, et al., Nucleic Acids Res. 16:1203, 1988), and FIG. 1 illustrates the construction of the expression plasmids pCaHj431, pCaHj432, pCaHj433, and pCaHj434 further described in Example 1.

DETAILED DESCRIPTION OF THE INVENTION

The amino acid sequence of the protein disulfide isomerase of the invention, which was isolated from a strain of the *A. oryzae*, has been aligned with that of protein disulfide isomerases of other origins and have been shown to have a degree of identity of about 38% with that of *Saccharomyces cerevisiae* (GenBank Acc. No. M62815) and 30% with that of Alfalfa (GenBank Acc. No. 11499).

These homologies are taken to indicate that some kind of evolutionary relationship exists between protein disulfide isomerases, and that the protein disulfide isomerase of the invention may represent a distinct class of protein disulfide isomerase. It is contemplated that the protein disulfide isomerase of the invention or DNA encoding the protein disulfide isomerase may be isolated from other organisms, including animals, especially a mammal, an insect, a plant or a microorganism. In the present context, especially interesting origins are bacteria and fungi, including yeasts and filamentous fungi.

As indicated above the sequence of the isolated enzyme shows that the protein disulfide isomerase of the invention has two -Cys-X-Y-Cys- subunits in positions 58–61 and 393–396.

The invention consequently also comprises active truncated forms of the enzymes of the invention, wherein at least one subunit is retained. Examples hereof could be an enzyme having an amino acid sequence corresponding to the residues 20 to 100, residues 330 to 450, or residues 360 to 430 of the appended SEQ ID No. 3, or the corresponding sequence of the enzyme of the invention in question.

Under this aspect, the invention specifically relates to enzymes exhibiting protein disulfide isomerase activity comprising the amino acid residues 1–131 (SEQ ID No. 10), 1–141 (SEQ ID No.9), 1–143 (SEQ ID No. 8), 1–163 (SEQ ID No. 7), 1–174 (SEQ ID No. 6), 1–281 (SEQ ID No. 5), or 25–225 (SEQ ID No. 12) of the amino acid sequence shown in the appended SEQ ID No. 3, or variants/derivatives thereof exhibiting a protein disulfide isomerase activity. Further specific enzymes are enzymes exhibiting protein disulfide isomerase activity comprising the amino acid residues 1–115, of the amino acid sequence shown in the appended SEQ ID No. 3 extended with the following sequence:

Leu-Ile-Arg-Glu-Leu-Leu-Gln-Glu-Leu-Val-Asn-Lys-His-Leu (SEQ ID No. 11); and an enzyme comprising the amino acid residues 1–511, of the amino acid sequence shown in the appended SEQ ID No. 3, and wherein the amino acid residue in position 511 is changed from Glu to Ala (SEQ ID No. 4).

The DNA sequence of the DNA construct of the invention encoding a recombinant protein disulfide isomerase enzyme as defined above is preferably as shown in the appended SEQ ID No. 1 (genomic DNA) or SEQ ID No. 2 (cDNA). Analogues of said sequences, which differ in one or more codons, but which encodes the recombinant protein disulfide isomerase are also within the invention.

Similar DNA sequences coding for the truncated forms of the protein disulfide isomerases of the invention are also part of the invention. DNA sequences therefore can be taken from SEQ ID No. 1, or preferably SEQ ID No. 2.

The DNA sequence of the DNA construct of the invention may be isolated by well-known methods. Thus, the DNA sequence may, for instance, be isolated by establishing a cDNA or genomic library from an organism expected to harbour the sequence, and screening for positive clones by conventional procedures. Examples of such procedures are hybridization to oligonucleotide probes synthesized on the basis of the full amino acid sequence shown in SEQ ID No. 3, or a subsequence thereof in accordance with standard techniques (cf. Sambrook et al., 1989), and/or selection for clones expressing a protein disulfide isomerase activity as defined above, and/or selection for clones producing a protein which is reactive with an antibody raised against the protein disulfide isomerase comprising the amino acid sequence shown in SEQ ID No. 3 and in particular amino acid residues 1–143 thereof as shown in SEQ ID No. 8.

A preferred method of isolating a DNA construct of the invention from a cDNA or genomic library is by use of polymerase chain reaction (PCR) using degenerate oligonucleotide probes prepared on the basis of the amino acid sequence of the protein disulfide isomerase of the invention comprising amino acid residues 1–515 of SEQ ID No. 3. For instance, the PCR may be carried out using the techniques described in U.S. Pat. No. 4,683,202 or by R. K. Saiki et al. (1988).

Alternatively, the DNA sequence of the DNA construct of the invention may be prepared synthetically by established standard methods, e.g. the phosphoamidite method described by Beaucage and Caruthers (1981), or the method described by Matthes et al. (1984). According to the phosphoamidite method, oligonucleotides are synthesized, e.g. in an automatic DNA synthesizer, purified, annealed, ligated and cloned in appropriate vectors.

Finally, the DNA construct may be of mixed genomic and synthetic, mixed synthetic and cDNA or mixed genomic and cDNA origin prepared by ligating fragments of synthetic, genomic or cDNA origin (as appropriate), the fragments corresponding to various parts of the entire recombinant DNA molecule, in accordance with standard techniques.

DNA constructs coding for the truncated forms of the enzyme of the invention may naturally be made in corresponding ways.

The recombinant expression vector carrying the DNA construct of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA construct of the invention, especially in a bacterial host, are the promoter of the lac operon of *E. coli,* the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus Amyloliquefaciens* α-amylase (amyQ), the promoters of the Bacillus subtilis xylA and xylB genes etc. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable a-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the recombinant protein disulfide isomerase of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis,* or one which confers antibiotic resistance such as ampicillin, kanamycin, chloramphenicol or tetracyclin resistance. Examples of Aspergillus selection markers include amdS, argB, niaD and sC, a marker giving rise to hygromycin resistance. Furthermore, the selection may be accomplished by co-transformation, e.g. as described in WO 91/17243.

While intracellular expression may be advantageous in some respects, e.g. when using certain bacteria as host cells, it is generally preferred that the expression is extracellular. The protein disulfide isomerase of the invention or truncated forms thereof comprising the amino acid sequences shown in the SEQ ID Nos. 3 to 12 may furthermore comprise a preregion permitting secretion of the expressed protein disulfide isomerase into the culture medium. If desirable, this preregion may be native to the protein disulfide isomerase of the invention or substituted with a different preregion or signal sequence, conveniently accomplished by substitution of the DNA sequences encoding the respective preregions.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. (1989)).

The cell of the invention either comprising a DNA construct or an expression vector of the invention as defined above is advantageously used as a host cell in the recombinant production of a polypeptide of the invention. The cell may be transformed with the DNA construct of the invention, conveniently by integrating the DNA construct in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal, an avian, an insect, or a plant cell, but is preferably a microbial cell, e.g. a bacterial or a fungal (including yeast) cell.

Examples of suitable bacteria are gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or gram negative bacteria such as *E. coli.* The transformation of the bacteria may for instance be effected by protoplast transformation or by using competent cells in a manner known per se.

The yeast organism may favourably be selected from a species of Saccharomyces or Schizosaccharomyces, e.g. *Saccharomyces cerevisiae.* The filamentous fungus may advantageously belong to a species of Aspergillus, e.g. *Aspergillus oryzae* or *Aspergillus niger.* Alternatively, a strain of a Fusarium species, e.g. *F. oxysporum,* can be used as a host cell. Fungal cells may be. transformed by a process involving protoplast formation and transformation of the protoplasts followed by regeneration of the cell wall in a manner known per se. A suitable procedure for transformation of Aspergillus host cells is described in EP 238 023. A suitable method of transforming Fusarium species is described by Malardier et al., 1989.

In a yet further aspect, the present invention relates to a method of producing a recombinant protein disulfide isomerase of the invention, which method comprises cultivating a host cell as described above under conditions conducive to the production of the protein disulfide isomerase and recovering the protein disulfide isomerase from the cells and/or culture medium.

The medium used to cultivate the cells may be any conventional medium suitable for growing the host cell in question and obtaining expression of the protein disulfide isomerase of the invention. Suitable media are available from commercial suppliers or may be prepared according to published recipes (e.g. in catalogues of the American Type Culture Collection).

The resulting protein disulfide isomerase may be recovered from the medium by conventional procedures including separating the cells from the medium by centrifugation or filtration, if necessary after disruption of the cells, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

It is of course also possible to produce the protein disulfide isomerases of the invention by culturing the filamentous fungal natural host or parent organism of interest and recovering the protein disulfide isomerase from the culture broth in traditional ways.

The present invention also relates to compositions comprising the protein disulfide isomerase of the invention.

The compositions may suitably contain 0.01–200 mg of enzyme protein per gram, preferably 0.01–20 mg of enzyme protein per gram, especially 0.01–2 mg of enzyme protein per gram, or alternatively 0.02–0.2 mg of enzyme protein per gram, or 0.01–0.2 mg of enzyme protein per gram.

The compositions of the invention may contain other ingredients known in the art as e.g. excipients, stabilizers, fillers, detergents, etc.

The compositions of the invention may be formulated in any convenient form, e.g. as a powder, paste, liquid or in granular form. The enzyme may be stabilized in a liquid by inclusion of enzyme stabilizers. Usually, the pH of a solution of the composition of the invention will be 5–10 and in some instances 7.0–8.5. Other enzymes such as proteases, cellulases, oxidases, peroxidases, amylases or lipases may be included in the compositions of the invention, either separately or in a combined additive.

The compositions of the invention can be used for the treatment or degradation of scleroproteins, especially hair, skin and wool, dehairing and softening of hides, treatment and cleaning of fabrics, as additives to detergents, thickening and gelation of food and fodder, strengthening of gluten in bakery or pastry products, and as pharmaceuticals for the alleviation of eye sufferings.

The present invention is further illustrated in the following examples which should not, in any manner, be considered to limit the scope of the present invention.

Materials and Methods

Strains

*Aspergillus oryzae* IFO 4177 available from Institute for Fermentation, Osaka; 17–25 Juso Hammachi 2-Chome Yodogawa-Ku, Osaka, Japan.

*Aspergillus niger* A524 (ATCC 16882)

*Aspergillus niger* TSA 1.

*E. coli* DH5αF'

Determination of PDI Activity

The PDI is assayed using the insulin reduction assay described by James et al., Cell 67:581–589, 1991.

Plasmids pUC 19, pMT 1560, pToC 90

EXAMPLES

Example 1

Cloning of *Aspergillus oryzae* and *Aspergillus niger* PDI Encoding Genes 1.1. Design of Oligo Nucleotides for PCR Amplification PDI from different organisms are highly homologous especially near the active site residues. In FIG. 1, the following 7 PDI gene products are aligned:

Bovine (*Bos taurus*) PDI (Yamauchi et al., Biochem. Biophys. Res. Commun. 146:1485–1492, 1987), Chicken (*Gallus gallus*) PDI (Parkkonen et al., Biochem. J. 256:1005–1011, 1988), Human (*Homo sapiens*) PDI (Rapilajaniemi et al. EMBO J. 6:643–649, 1987), Mouse (*Mus musculus*) PDI (Gong, et al., Nucleic Acids Res. 16:1203, 1988), Rabbit (*Oryctolagus cuniculus*) PDI (Fliegel et al., J. Biol. Chem. 265:15496–15502, 1990), Rat (*Rattus norvegicus*) PDI (Edman et al., Nature 317:267–270, 1985), Yeast (*Saccharomyces cerevisiae*) PDI (Tachikawa et al., J. Biochem. 110:306–313).

Each subunit contains two active centres (Freedman et al., Cell 57:1069–1072, 1989) and the homology in the surroundings of these active centres are particularly strong. A consensus amino acid sequence for the active centre closest to the N-terminus was determined from the alignment as -APWCGHCK-, and an oligo aeoxyribonucleotide encoding the peptide -WCGHCK- and extended with an EcoRI site in the 5' end, was synthesized:

5' TGGAATTCTGGTGYGGNCAYTGYAA3' (primer 4762, 25 nucleotides, 32 species, SEQ ID No. 13)
(Y=C or T; R=A or G; N=A, T, C, or G).

A consensus amino acid sequence for the active centre closest to the C-terminus was determined: -YAPWCGHCK-, and an oligo deoxyribonucleotide encoding the peptide -YAPWCG- in antisense and extended with a BamHI site in the 5' end was synthesized:

5' TGGGATCCRCACCANGGNGCRTA3' (primer 4763, 23 nucleotides, 64 species, SEQ ID NO. 14).

These oligo deoxyribonucleotides (primers 4762 and 4763) were used as primers in a PCR reaction to amplify PDI-encoding gene fragments from genomic DNA from *A. oryzae* and *A. niger.*

1.2 Amplification and Cloning of Fragments of PDI-encoding Genes

Genomic DNA was prepared from *Aspergillus oryzae* IFO 4177 and *Aspergillus niger* A524 as described by Yelton et al. (Proc. Natl. Acad. Sci. USA 81:1470–1474, 1984).

PCR reaction mixtures contained Taq DNA polymerase buffer supplied by Clontech laboratories Inc. and diluted as described, 250 μM of each of dATP, dCTP, dGTP, and, dTTP, 100 pmol of each of primers 4762 and 4763, and 0.5 μg of genomic DNA of either *A. niger* or *A. oryzae.* The total reaction volume was 0.1 ml, and it was covered with 0.05 ml paraffin oil.

The following program was run on a Cetus Perkin Elmer thermal cycler:

1. cycle: 94° C. for 2 min., (when the temperature reached 94° C. 2.5 U of Taq DNA polymerase supplied by Clontech laboratories Inc. was added).

10 cycles: 94° C. for 1 min., 50° C. for 1 min., and 72° C. for 2 min.

30 cycles: 94° C. for 1 min., 55° C. for 1 min., and 72° C. for 2 min.

1 cycle: 72° C. for 5 min.

The reaction mixtures were loaded on an agarose gel, and both the A. oryzae and the A. niger DNA produced fragments of approximately 1.1 kb.

The fragments were digested with EcoRI and BamHI and ligated to pUC19 (Yanisch-Perron et al., Gene 33:103–119, 1985). The ligation mixture was transformed into E. coli DH5αF' (Woodcock et al., Nucleic Acids Res. (1989) 17:3469–3478). Recombinant plasmids were subjected to sequence analysis using the Sequenase™ kit (United States Biochemical) and a M13 universal primer following the manufacturers instructions. The analysis confirmed that both in the case of A. oryzae and in that of A. niger sequences homologous to other PDI genes were amplified and cloned.

1.3 Genome Cloning of the A. oryzae PDI-encoding Gene

Genomic DNA from A. oryzae was digested with the following restriction enzymes supplied by New England Biolabs Inc.: HindIII, BamHI, BamHI+HindIII, EcoRI, EcoRI+HindIII, SalI, SalI+HindIII, BglII, BglII+HindIII, PstI and PstI+HindIII. After digestion, the reaction mixtures were run on a 1% agarose gel and then blotted onto an Immobilon N™ membrane (Millipore Corporation) following the manufacturers instructions. The membrane was probed with the cloned A. oryzae PCR product isolated as a BamHI-EcoRI fragment and radio labelled with $^{32}$p, After stringent washes the membrane was subjected to autoradiography.

Genomic DNA from A. niger was digested with the following restriction enzymes: BglII, BamHI, BamHI+BglII, EcoRI, EcoRI+BglII, SalI, SalI+BglII, HindIII, HindIII+BglII, PstI and PstI+BglII. The Southern blot was made as described with A. oryzae, only the A. niger PCR product was used as probe.

1.4 Construction of Genomic A. oryzae Library

Southern analysis indicated that the A. oryzae PDI gene was located on a 6.8 kb BglII fragment. Genomic A. oryzae DNA was digested with BglII and fragments ranging from 5 kb to 8.5 kb were isolated from an agarose gel. Subcloning thereof and Southern analysis indicated that the A. oryzae PDI gene was located on a 2.3 kb BamH I, Hind III fragment. Genomic A. oryzae DNA was digested with BamH I and Hind III and fragments ranging from 1.9–3 kb were isolated from an agarose gel. This mixture of fragments was ligated to pUC19 digested with BamHI and Hind III. The ligation mixture was used to transform E. coli DH5αF'. The transformed E. coli cells were spread onto 10 agar plates using ampicillin selection.

1.5 Screening of the A. oryzae Genomic Library

The libraries were screened using the filter colony hybridization method described by Gergen et al. (Nucleic Acids Res. 7:2115–2136, 1979). The probe that was used for the Southern blot was also used for the colony hybridization. Positive clones were isolated and confirmed by sequence analysis using sequencing primers designed from the sequences of the PDI fragments. One of the plasmids containing the desired fragment was termed pCaHj 425.

1.6 Sequence of the Gene

The gene was sequenced using the Taq DyeDeoxy™ Terminator cycle sequencing kit supplied by Applied Biosystems following the manufacturer's instructions. The sequence reactions were run on an Applied Biosystems 373A DNA sequencer and the data were evaluated using the Macintosh computer program SegEd version 1.0 supplied by Applied Biosystems.

The sequence of the A. oryzae gene is shown in the appended SEQ ID No 1.

The amino acid composition of the purified PDI obtained as described in Example 2 was in accordance with the composition deduced from the DNA-sequence shown in SEQ ID No. 1. From homology to other PDI genes and consensus splicing sequences a CDNA sequence as shown in SEQ ID no. 2 was suggested. The derived protein sequence is as shown in SEQ ID No. 3.

Example 2

Expression of Truncated Forms of the A. oryzae PDI Gene 2.1 Construction of Expression Plasmids The PDI gene of A. oryzae was truncated at various positions by introduction stop codons. This was done by PCR amplification of the PDI gene using a 5' PCR primer harbouring a BamH I site at its 5' end and 8 different 3' primers corresponding to 8 different truncations each harbouring a Hind III site. The sequence of the 5' primer was:

```
5' TTCGGATCCACCATGCGGACTTTCGCACC 3'           5205. (SEQ ID No. 15)

The sequences of the eight 3'primers were:

5' CCAAGCTTTAGAGATGCTTGTTGACAAGCTCCTG
   GAGGAGCTCCCTGATAAGCTT 3'                  5215. (SEQ ID No. 16)

5' CCAAGCTTTAGACCATGTATGACACAATCGCCTCG
   GTCTGACGAG 3'                             5397. (SEQ ID No. 17)

5' CCAAGCTTTAGACAGGGGACACAGCAGGTAG 3'        5895. (SEQ ID No. 18)

5' CCAAGCTTTATGGGGTGACAGGGGACA 3'            5399. (SEQ ID No. 19)

5' CCAAGCTTTAAGACGCGATATAACCAATAAC 3'        5894. (SEQ ID No. 20)

5' CCAAGCTTTAAGTGGTGAATATATCATTGGC 3'        5893. (SEQ ID No. 21)

5' CCAAGCTTAGTGTTTCTCGGCGATGAACTT 3'         6314. (SEQ ID No. 22)

5' CCAAGCTTTACGCAGACTTGTCATCGCTAGT 3'        5204. (SEQ ID No. 23)
```

Primer 5215 directed an extension of the PDI gene amino acid 1–115 with the sequence Leu-Ile-Arq-Glu-Leu-Leu-Gln-Glu-Leu-Val-Asn-Lys-His-Leu (SEQ ID NO. 11): followed by a stop codon.

Primer 5397 introduced a stop codon after amino acid 131.

Primer 5895 introduced a stop codon after amino acid 141.

Primer 5399 introduced a stop codon after amino acid 143.
Primer 5894 introduced a stop codon after amino acid 163.
Primer 5893 introduced a stop codon after amino acid 174.
Primer 6314 introduced a stop codon after amino acid 281.
Primer 5204 introduced the mutation E511A (meaning substituting and a stop codon after amino acid 511.

The expression plasmids were constructed by PCR amplification using primer 5205 in combination with either 5215, 5397, 5895, 5399, 5894, 5893, 6314 or 5204 and pCaHj 425 as template using standard PCR conditions. The generated PCR fragments were digested with BamH I and Hind III and inserted into pMT 1560 (described in e.g. PCT/DK94/00138) digested with the same enzymes (See FIG. 3). The constructed plasmids were named pCaHj 432 (from primer 5215), pCaHj 433 (from primer 5397), PCaHj 441 (from primer 5895), pCaHj 434 (from primer 5399), pCaHj 440 (from primer 5894), pCaHj 439 (from primer 5893), pCaHj 445 (from primer 6314) and pCaHj 431 (from primer 5204).

2.2 Transformation of *A. oryzae* IFO 4177

Each of the plasmids pCaHj 432, pCaHj 433, PCaHj 441, pCaHj 434, pCaHj 440, pCaHj 439, pCaHj 445 and pCaHj 431 were transformed into *A. oryzae* IFO 4177 by cotransformation with the amds selection plasmid pToC 90 (described in WO91/17243) following the procedure described in the published EP patent application No. 238 023.

A number of transformants of each plasmid were evaluated.

2.3 Transformation of *A. niger* TSA 1

Each of the plasmids PCaHj 441, pCaHj 434, pCaHj 440 and pCaHj 439 were transformed into *A. niger* TSA 1 by the same procedure as with *A. oryzae*.

A number of transformants of each plasmid were evaluated.

Example 3
Fermentation Purification and Characterization of the *Aspergillus oryzae* PDI Truncations 3.1 *A. oryzae* IFO 4177 Transformants Crude truncated PDI preparation was isolated from supernatants obtained by fermentation of the *A. oryzae* or *A. niger* pCaHj 432, pCaHj 433, PCaHj 441, pCaHj 434, pCaHj 440, pCaHj 439, pCaHj 445 or pCaHj 431 transformants in shake flasks containing YPM medium (1 liter: 5 g Difco Yeast extract, 10 g Difco peptone, 20 g maltose). The supernatant was recovered by filtration. The PDI truncation gene products were partially purified using a 1 ml HiTrap Q™ anion exchanger from Pharmacia LKB Biotechnology AB Uppsala, Sweden following the manufacturers instructions. Fractions were collected and analyzed by measuring the disulphide isomerase activity and by SDS PAGE.

The pCaHj 434 transformants secreted a protein of approx 14 kD (SDS PAGE) not present in supernatants of the untransformed strain. Enrichment of this protein by ion exchange was followed by increased disulphide isomerase activity. The approx. 14 kD band was blotted from an SDS Page gel and subjected to N-terminal amino acid sequence determination using an Applied Biosystems 473A protein sequencer. A sequence of 7 amino acids could unambiguously be determined as: Thr-Ala-Glu-Ala-Pro-Ser-Asp. This sequence corresponds to residue 24–30 of the *A. oryzae* protein sequence. The size of the truncation expected from the amino acid sequence is thus 13.2 kD. So it can be concluded that the pCaHj 434 gene product is secreted to the supernatant, that it has the expected size and that it is catalytic active.

The pCaHj 441 transformants secreted a protein of the same size as the pCaHj 434 transformants. Also for this truncation enrichment of the protein was followed by increased disulphide isomerase activity demonstrating that the pCaHj 441 gene product is a catalytic active secreted protein.

The pCaHj 440 transformants secreted a protein of approx 16 kD not present in the untransformed strain. The expected size is 15.7 kD assuming the same N-terminal sequence as the pCaHj 434 product. Enrichment of the protein by ion exchange was followed by increased disulphide isomerase activity demonstrating that also the pCaHj 440 gene product is a catalytic active secreted protein.

The pCaHj 445 transformants secreted a protein of approx 30 kD not present in the untransformed strain. The expected size is 28.6 kD assuming the same N-terminal sequence as the pCaHj 434 product. Enrichment of the protein by ion exchange was followed by increased disulphide isomerase activity demonstrating that the pCaHj 440 gene product is a catalytic active secreted protein.

3.2 *A. niger* TSA 1 Transformants

Transformants of PCaHj 441, pCaHj 434, pCaHj 440 and pCaHj 439 were evaluated in the same way as the corresponding *A. oryzae* transformants with the exception that the N-terminal amino acid sequence was not determined for any of the proteins secreted by *A. niger*.

In all other aspects the same results were obtained with the *A. niger* transformants as with the *A. oryzae* transformants. However the fermentation yield of the truncations were generally lower in *A. niger* than in *A. oryzae*.

TABLE 1

```
           1                                                        50
Pdi_Mouse  .......MLS RALLCLALAW AARVGADALE EEDNVLVLKK SNFEEALAAH
Pdi_Rat    .......MLS RALLCLAAAW AARVGADALE EEDNVLVLKK SNFAEALAAH
Pdi_Bovin  .......MLR RALLCLALTA LFRAGAGAPD EEDHVLVLHK GNFDEALLAH
Pdi_Human  .......MLR RALLCLAVAA LVR..ADAPE EEDHVLVLRK SNFAEALAAH
Pdi_Rabit  .......MLR RAVLCLALAV TA.GWAWAAE EEDNVLVLKS SNFAEELAAH
Pdi_Chick  .......... .......... ......EPLE EEDGVLVLRA ANFEQALAAH
Pdi_Yeast  MKFSAGAVLS WSSLLLASSV FAQQEAVAPE DSA.VVKLAT DSFNEYIQSH 51                                                       100
Pdi_Mouse  KYLLVEFYAP WCGHCKALAP EYAKRAAKLK AEGSEIRLAK VDATEESDLA
Pdi_Rat    NYLLVEFYAP WCGHCKALAP EYAKAAAKLK AEGSEIRLAK VDATEESDLA
Pdi_Bovin  KYLLVEFYAP WCGHCKALAP EYAKAAGKLK AEGSEIRLAK VDATEESDLA
Pdi_Human  KYLLVEFYAP WCGHCKALAP EYAKAAGKLK AEGSEIRLAK VDATEESDLA
Pdi_Rabit  KHLLVEFYAP WCGHCKALAP EYAKAAGKLK AEGSDIRLAK VDATEESDLA
Pdi_Chick  RHLLVEFYAP WCGHCKALAP EYAKAAAQLK AEGSEIRLAK VDATEEAELA
Pdi_Yeast  DLVLAEFFAP WCGHCKNMAP EYVKAAETL. .VEKNITLAQ IDCTENQDLC
```

TABLE 1-continued

```
            101                                              150
Pdi_Mouse   QQYGVRGYPT IKFFKNGDTA SPKEYTAGRE ADDIVNWLKK RTGPAATTLS
Pdi_Rat     QQYGVRGYPT IKFFKNGDTA SPKEYTAGRE ADDIVWWLKK RTGPAATTLS
Pdi_Bovin   QQYGVRGYPT IKFFKNGDTA SPKEYTAGRE ADDIVNWLKK RTGPAASTLS
Pdi_Human   QQYGVRGYPT ZKFFRNGDTA SPKEYTAGRE ADDIVNWLKK RTGPAATLLR
Pdi_Rabit   QQYGVRGYPT ZKFFKNGDTA SPKEYTAGRE ADDIVNWLKK RTGPAATTLA
Pdi_Chick   QQFGVRGYPT ZKFFRNGDKA APREYTAGRE ADDIVSWLKK RTGPAATTLT
Pdi_Yeast   MEHNIPGFPS LKIFKNSDVN NSIDYEGPRT AEAIVQFMIK QSQPAVAVVA 151                                              200
Pdi_Mouse   DTAAAESLVD SSEVTVIGFF KDVESDSAKQ FLLAAEAIDD IPFGITSNSG
Pdi_Rat     DTAAAESLVD SSEVTVIGFF KDAGSDSAKQ FLLAAEAVDD IPFGITSNSD
Pdi_Bovin   DGAAAEALVE SSEVAVIGFF KDMESDSAKQ FFLAAEVIDD IPFGITSNSD
Pdi_Human   DGAAAESLVE SSEVAVZGFF KDVESDSAKQ FLQAAZAZDD IPFGITSNSD
Pdi_Rabit   DSAAAESLVE SSEVAVZGFF KDVESDAAKQ FLLAAEATDD IPFGITSNSD
Pdi_Chick   DAAAAETLVD SSEVVVIGFF KDVTSDAAKE FLLAAESVDD IPFGISSSAD
Pdi_Yeast   DLPAYLANET FVTPVIVQSG KIDADFNATF YDFVSAENAD YDFVSAENAD 201                                              250
Pdi_Mouse   VFSKYQLDKD GVVLFKKFDE GR..NNFEGE ITKEKLLD.F IKHNQLPLVI
Pdi_Rat     VFSKYQLDKD GVVLFKKFDE GR..NNFEGE ITKEKLLD.F IKHNQLPLVI
Pdi_Bovin   VFSKYQLDKD GVVLFKKFDE GR..NNFEGE VTKEKLLD.F IKHNQLPLVI
Pdi_Human   VFSKYQLDKD GVVLFKKFDE GR..NNFEGE VTKENLLD.F IKHNQLPLVI
Pdi_Rabit   VFSRYQVHQD GVVLFKKFDE GR..NNFEGE VTKEKLLD.F IKHNQLPLVI
Pdi_Chick   VFSKYQLSQD GVVLFKKFDE GR..NNFEGD LTKDNLLN.F IKSNQLPLVI
Pdi_Yeast   ..DDFKL... SIYLPSAMDE PVVYNGKKAD IADADVFEKW LQVEALPYFG 251                                              300
Pdi_Mouse   EFTEQTAPKI FGGEIKTHIL LFLPKSVSDY DGKLSSFKRA AEGF..KGKI
Pdi_Ra      EFTEQTAPKI FGGEZKTHIL LFLPKSVSDY DGKLSNFKKA AEGF..KGKI
Pdi_Bovin   EFTEQTAPKI FGGEIKTHIL LFLPKSVSDY EGKLSNFKKA AESF..KGKI
Pdi_Human   EFTEQTAPKI FGGEIKTHIL LFLPKSVSDY DGKLSNFKTA AESF..KGKI
Pdi_Rabit   EFTEQTAPKI FGGEIKTHIL LFLPRSAADH DGKLSGFKQA AEGF..KGKI
Pdi_Chick   EFTEQTAPKI FGGEIKTHIL LFLPKSVSDY EGKLDNFKTA AGNF..KGKI
Pdi_Yeast   EIDGSVFAQY VESGLPLGLY FY......ND EEELEEYKPL FTELAKKNRG 301                                              350
Pdi_Mouse   LFIFIDSDHT DNQRILEFFG LKKEECPAVR LITLEEEM.. .......TKY
Pdi_Rat     LFIFIDSDHT DNQRILEFFG LKKEECPAVR LITLEEEM.. .......TKY
Pdi_Bovin   LFIFIDSDHT DNQRILEFFG LKKEECPAVR LITLEEEM.. .......TKY
Pdi_Human   LFIFIDSDHT DNQRILEFFG LKKEECPAVR LITLEEEM.. .......TKY
Pdi_Rabit   LFIFIDSDHT DNQRILEFFG LKKEECPAVR LITLEEEM.. .......TKY
Pdi_Chick   LFIFIDSDHT DNQRILEFFG LKKEECPAVR LITLEEEM.. .......TKY
Pdi_Yeast   LMNFVSIDAR KFGRMAGNLN M.KEQFPLFA IHDMTEDLKY GLPQLSEEAF 351/////////////////////////////////////////////400
Pdi_Mouse   KPESDELTAE K..ITEFCHR FLEGKIKPHL MSQEVPEDWD KQPVKVLVGA
Pdi_Rat     KPESDELTAE K..ITQFCHH FLEGKIKPHL MSQELPEDWD KQPVKVLVGK
Pdi_Bovin   KPESDELTAE K..ITEFCHR FLEGKIKPHL MSQELPDDWD KQPVKVLVGK
Pdi_Human   KPESEELTAE R..ITEFCHR FLEGKIKPHL MSQERAGDWD KQPVKVPVGK
Pdi_Rabit   KPESDELTAE G..ITEFCQR FLEGKIKPHL MSQELPEDWD RQPVKVLVGK
Pdi_Chick   KPESDDLTAD K..IKEFCNK FLEGKIKPHL MSQDLPEDWD KQPVKVLVGK
Pdi_Yeast   DELSDKZVLE SKAIESLVKD FLKGDASPZV KSQEIFENQD S.SVFQLVGK 401                                              450
Pdi_Mouse   NFEEAAFDEK KNVFVEFYAP WCGHCKQLAP IWDKLGETY. KDHENIIIAK
Pdi_Rat     NFEEVAFDEK KNVFVEFYAP WCGHCKQLAP IWDKLGETY. KDHENIIIAK
Pdi_Bovin   NFEEVAFDEK KNVFVEFYAP WCGHCKQLAP IWDKLGETY. KDHENIIIAK
Pdi_Human   NFEDVAFDEK KNVFVEFYAP WCGHCKQLAP IWDKLGETY. KDHENIIIAK
Pdi_Rabit   NFEEVAFDEK KNVFVEFYAP WCGHCKQLAP IWDKLGETY. KDHENIIIAK
Pdi_Chick   NFEEVAFDEN KNVFVEFYAP WCGHCKQLAP IWDKLGETY. KDHENIIIAK
Pdi_Yeast   NHDEIVNDPK KNVFVEFYAP WCGHCKQLAP IWDKLGETY. KDHENIIIAK 451                                              500
Pdi_Mouse   MDSTANEVEA VKVHSFPTLK FFPASADRTV IDYNGERTLD GFKKFLESGG
Pdi_Rat     MDSTANEVEA VKVHSFPTLK FFPASADRTV IDYNGERTLD GFKKFLESGG
Pdi_Bovin   MDSTANEVEA VKVHSFPTLK FFPASADRTV IDYNGERTLD GFKKFLESGG
Pdi_Human   MDSTANEVEA VKVHSFPTLK FFPASADRTV IDYNGERTLD GFKKFLESGG
Pdi_Rabit   MDSTANEVEA VKVHSFPTLK FFPASADRTV IDYNGERTLD GFKKFLESGG
Pdi_Chick   MDSTANEVEA VKVHSFPTLK FFPASADRTV IDYNGERTLD GFKKFLESGG
Pdi_Yeast   LDHTENDVRG VVIEGYPTIV LYPGGKKSES VVYQGSRSLD SLFDFIKENG 501                       538
Pdi_Mouse   QDGAGDDEDL .DLEE..ALE PDMEE..DDD QKAVKDEL
Pdi_Rat     QDGAGDNDDL .DLEE..ALE PDMEE..DDD QKAVKDEL
Pdi_Bovin   QDGAGDDDDL EDLEE..AEE PDLEE..DDD QKAVKDEL
Pdi_Human   QDGAGDDDDL EDLEE..AEE PDMEE..DDD QKAVKDEL
```

TABLE 1-continued

```
Pdi_Rabit  QDGAGDEDGL EDLEE..AEE PDLEE..DDD QKAVRDEL
Pdi_Chick  QDGAAADDDL EDLET..DEE TDLEEGDDDE QKIQKDEL
Pdi_Yeast  HFDVDGKALY EEAQEKAAEE ADADAELADE EDAIHDEL
```

TABLE 2

```
Alfalfa  M-AKNVAIFG LLFSLLLLVP SQIFA----- -------EES STDAKE----
Oryzae   MRTFAPWIL- --SLLGASA- --VAS----- ------AADA TAEAPS----
Yeast    MKFSAGAVLS WSSLLLASS- --VFA----- ------QQEA VAPEDS----
Bovine   M-LRRA-LLC --LALTALF- --RVG----- -------AGA PDEEDH----
Rat      M-LSRA-LLC --LALAWAA- --RVG----- -------ADA LEEEDN----
Mouse    MKLRKAWLLV LLLALTQLLA AASAGDAQED TSDTENATEE EEEEDDDDLE ---------- ---------- ----FVL--- ---------- ----------
         ---------- ---------- ----DVV--- ---------- ----------
         ---------- ---------- ----AVV--- ---------- ----------
         ---------- ---------- -----VL--- ---------- ----------
         ---------- ---------- -----VL--- ---------- ----------
         VKEENGVWVL NDGNFDNFVA DKDTVLLEFY APWCGHCKQF APEYEKIAST ---------- ---------- ---------- ----TLDNT- ----------
         ---------- ---------- ---------- ----SLTGD- ----------
         ---------- ---------- ---------- ----KLATD- ----------
         ---------- ---------- ---------- ----VLHKG- ----------
         ---------- ---------- ---------- ----VLKKS- ----------
         LKDNDPPIAV AKIDATSASM LASKFDVSGY PTIKILKKGQ AVDYDGSRTQ ---------- ---------- --------NF HDTVKKHDFI VVEFYAPWCG
         ---------- ---------- --------TF ETFVKEHDLV LAEFFAPWCG
         ---------- ---------- --------SF NEYIQSHDLV LAEFFAPWCG
         ---------- ---------- --------NF DEALAAHKYL VEFY-APWCG
         ---------- ---------- --------NF AEPAAHNYLL VEFY-APWCG
         EEIVAKVREV SQPDWTPPPE VTLSLTKDNF DDVVNNADII LVEFYAPWCG HCKKLAPEYE KAASILSTHE PPVVLAKVDA NEEHNKDLAS ENDVKGFPTI
         HCKALAPEYE QAATELKEKN IPL--VKVDC TEEEA--LCR DQGVEGYPTL
         HCKNMAPEYV KAAETLVEKN ITL--AQIDC TENQD--LCM EHNIPGFPSL
         HCKALAPEYA KAAGKLKAEG SEIRLAKVDA TEESD--LAQ QYGVRGYPTI
         HCKALAPEYA KAAAKLKAEG SEIRLAKVDA TEESD--LAQ QYGVRGYPTI
         HCKKLAPEYE KAAKELSKRS PPIPLAKVDA TEQTD--LAK RFDVSGYPTL KIFRNGG-KN IQEYKGPREA EGIVEYLKKQ SGPAS-TEIK SADDATAFVG
         KIFRGLDAVK P--YQGARQT EAIVSYMVKQ SLPAV-SPVT DQGVEGYPTL
         KIFKNRDVNN SIDYEGPRTA EAIVQFMIKQ SQPAV-AVVA DLPAYL-ANE
         KFFKNGDTAS PKEYTAGREA DDIVNWLKKR TGPAA-STLS DGAAAEALVE
         KFFKNGDTAS PKEYTAGREA DDIVNWLKKR TGPAA-TTLS DTAAAESLVD
         KIFRKG---R PFDYNGPREK YGIVDYMIEQ SGPPSKEILT LKQVQEFLKD DNKVVIVGVG PKFSGEEYDN FIALAEKLRS DYDFAHTLNA KHLPKGDSSV
         MDKIVVIGYI ASDDQTANDI FTTFAESQRD NYLFAATSDA SI--AKAEGV
         TFVTPVIVQS GKIDADFNAT FYSMANKHFN DYDFVSAENA DD--DFKLSI
         SSEVAVIGFF KDMESDSAKQ FFLAAEVI-D DIPFGITSNS DV--FSKYQL
         SSEVTVIGFF KDAGSDSAKQ FLLAAEAV-D DIPFGITSNS DV--FSKYQL
         GDDVVIIGLF QGDGDPAYLQ YQDAANNLRE DYKFHHTFSP EIAKFLKVSL SGPVVRLFKP FDELFVDS-- -KDFNVEALE KFIEESSTPI VTVFNNEPSN
         KQPSIVLYKD FDEKKATYDG EIEQDALLSW VKTASTPLVG ELGPETYSGY
         YLPSAM--DE PVVYNGKKAD IADADVFEKW LQVEALPYFG EIDGSVFAQY
         DKDGVVLFKK FD---EGR-- -NNFEGEVTK EKLLDFIKHN QLPLVIEFTE
         DKDGVVLFKK FD---EGR-- -NNFEGEVTK EKLLDFIKHN QLPLVIEFTE
         GKLVLTHPEK FQSKYEPRFH VMDVQGSTEA SAIKDYVVKH ALPLVGHRKT HRFVVKFFNS PNAKAMLFIN FTTEGAESFK TKYHEVAEQY KQQGV-SFLV
         ITAGIPLAYI FAETKEEREQ FTEEFKFIAE KHKGSINIVT IDAKLYGAHA
         VESGLPLGYL FYNDEEELEE YKPLFTELAK KNRGLMNFVS IDARKFGRHA
         QTAPKIFGGE IKTHILLFLP KSVSDYDGKL SNFKKAAEGF KGKILFIFID
         QTAPKIFGGE IKTHILLFLP KSVSDYDGKL SNFKKAAEGF KGKILFIFID
         SNDAKRYSKR PLVVVYYSVD FSFDYRAATQ FWRNKVLEVA KDFPEYTFAI GDVESSQGAF QYFGLKEEQV PLI--IIQHN DGKKFFKPN- --LELDQLPT
         GNLNLDPSKF PAFAIQDPEK NAKY------ --PYDQSKE- --VKAKDIGK
         GNLNMK-EQF PLFAIHDMTE DLKYGLPQLS EEAFDELSDK IVLESKAIES
         SDHTDNQRIL EFFGLKKEEC PAVR-LITLE EEMTKYKPES DELTAEKITE
         SDHTDNQRIL EFFGLKKEEC PAVR-LITLE EEMTKYKPES DELTAEKITE
         ADEEDYATEV KDLGL-SESG EDVN-AAILD ESGKKFAMEP EEFDSDTLRE
```

TABLE 2-continued

```
WLKAYKDGKV EPFVKSEPIP ETNN-EPVKV VVGQTLEDVV FKSGKNVLIE
FIQDVLDDKV EPSIKSEAIP ETQE-GPVTV VVAHSYKDLV LDNEKDVLLE
LVKDFLKGDA SPIVKSQEIF ENQD-SSVFQ LVGKNHDEIV NDPKKDVLVL
FCHRFLEGKI KPHLMSQELP DDWDKQPVKV LVGKNFEEVA FDEKKNVFVE
FCHRFLEGKI KPHLMSQELP EDWDKQPVKV LVGKNFEEVA FDEKKNVFVE
FVTAFKKGKL KPVIKSQPVP KN-NKGPVKV VVGKTFDAIV MDPKKDVLIE

FYAPWCGHCK QLAPILDEVA VSFQS-DADV VIAKLDATAN DIPTDTFDVQ
FYAPWCGHCK ALAPKYEELA SLYKD-IPEV TIAKIDATAN DV--PD-SIT
YYAPWCGHCK RLAPTYQELA DTYANATSDV LIAKLDHTEN DV--RGVVIE
FYAPWCGHCK QLAPIWDKLG ETYKD-HENI VIAKMDSTAN EV--EAVKVH
FYAPWCGHCK QLAPIWDKLG ETYKD-HENI VIAKMDSTAN EV--EAVKVH
FYAPWCKHCK QLEPIYTSLG KKYKG-QKDL VIAKMDATAN DITNDQYKVE

GYPTLYFRSA SGK--LSQYD GGRTKEDIIE FIE------K NKDKTGAAHQ
GFPTIKLFAA GAKDSPVEYE GSRTVEDLAN FVK------E NGKHKVDALE
GYPTIVLYPG GKKSESVVYQ GSRSLDSLFD FIK------E NGHFDVDGKA
SFPTLKFFPA SADRTVIDYN GERTLDGFKK GLESGGQDGA GDDDDLEDLE
SFPTLKFFPA SADRTVIDYN GERTLDGFKK GLESGGQDGA GDDDDLEDLE
GFPTIYFAPS GDKKNPI--- ---------K F--------E GGNRDLEHLS

EVEQPKAAAQ PE-------- ---------- AEQPKDEL
VDPKKEQESG DATETRAASD ETETPAATSD DKSEHDEL
LYEEAQEKAA EEAEADAEAE ADADAELADE EDAIHDEL
EAEEPDLEED DD-------- ---------- QKAVKDEL
EAEEPDLEED DD-------- ---------- QKAVKDEL
KF--ID-EHA TK-------- ---------- RSRTKEEL
```

REFERENCES CITED IN THE SPECIFICATION

Sambrook, J., Fritsch, E. F. & Maniatis, T. 1989. Molecular Cloning: A Laboratory Manual. 2. edition. Cold Spring Harbor Lab., Cold Spring Harbor, N.Y.
U.S. Pat. No. 4,683,202.
Hudson et al, 1989, Practical Immunology, Third edition, Blackwell Scientific Publications.
Beaucage and Caruthers, 1981, Tetrahedron Letters 22, 1981, pp. 1859–1869.
Matthes et al., 1984, The EMBO J. 3, 1984, pp. 801–805.
R. K. Saiki et al., 1988, Science 239, pp. 487–491.
WO 91/17243.
EP 238 023.
Malardier et al. Gene 78 (1989), pp. 147–156.
Woodcock et al., Nucleic Acids Res. (1989) 17:3469–3478.

What is claimed is:

1. An isolated polypeptide having protein disulfide isomerase activity, which (a) is encoded by a nucleic acid sequence which hybridizes with (i) the DNA sequence of SEQ ID NO:1 or (ii) the DNA sequence of SEQ ID NO:2, under the following conditions: presoaking in 5×SSC and prehybridizing for 1 h at ~40° C. in a solution of 5×SSC, 5×Denhardt's solution, 50 mM sodium phosphate, pH 6.8, and 50 μg of denatured sonicated calf thymus DNA, followed by hybridization in the same solution supplemented with 50 μCi 32P-dCTP labelled probe for 18 h at ~40° C. followed by washing three times in 2×SSC, 0.2% SDS at 40° C. for 30 minutes; and (b) has an amino acid sequence that is at least 80% homologous to the amino acid sequence of SEQ ID NO:3.

2. The polypeptide of claim 1 having an amino acid sequence of SEQ ID NO: 3 or a fragment thereof that has protein disulfide isomerase activity.

3. The polypeptide of claim 1 having an amino acid sequence comprising amino acids 1–514 of SEQ ID NO:3 and extended with one Ala.

4. The polypeptide of claim 1, which is a filamentous fungal polypeptide.

5. The polypeptide of claim 4, which is an Aspergillus polypeptide.

6. The polypeptide of claim 5, which is an *Aspergillus oryzae* or *Aspergillus niger* polypeptide.

7. A composition comprising a polypeptide of claim 1.

8. The composition of claim 7, in the form of a non-dusting granulate, stabilized liquid or protected enzyme.

9. The composition of claim 7, which contains 0.01–200 mg of protein/g.

10. The composition of claim 7, which additionally comprises an amylase, cellulase, lipase, peroxidase and/or protease.

11. The composition of claim 7, which is a pharmaceutical composition.

12. A process for treating scleroproteins, which comprises applying the composition of claim 7 to the scleroprotein.

13. The process of claim 12, wherein the scleroprotein is human hair or skin; or animal hair or skin.

14. The process of claim 13, further comprising waving, straightening, removing, degrading or softening of the hair; or softening and/or restoration of the skin.

15. A process for dehairing and/or softening of hides, comprising applying the composition of claim 13 to the hides.

16. A process for the cleaning of fabrics, comprising applying the composition of claim 7 to the fabric.

17. The process of claim 16, further comprising applying a detergent to the fabric.

18. A process for thickening and/or gelation of food and/or fodder products, comprising applying the composition of claim 7 to the food or fodder.

19. A process for strengthening of gluten in bakery or pastry products, comprising applying the composition of claim 7 to the baked or pastry product.

20. A process for the treatment of eye conditions, comprising applying the composition of claim 7 to the eye.

21. An isolated nucleic acid sequence comprising a nucleic acid sequence which encodes the polypeptide of cliam 1.

22. A nucleic acid sequence of claim 21 comprising a DNA sequence of SEQ ID NO:1.

23. A nucleic acid sequence of claim 21 comprising a DNA sequence of SEQ ID NO:2.

24. A nucleic acid sequence of claim 21, wherein the polypeptide is a filamentous fungal polypeptide.

25. A nucleic acid sequence of claim 21, wherein the polypeptide is an Aspergillus polypeptide.

26. A nucleic acid sequence of claim 21, wherein the polypeptide is an *Aspergillus oryzae* or *Aspergillus niger* polypeptide.

27. A nucleic acid construct comprising the nucleic acid sequence of claim 23 operably linked to one or more control sequences that direct the production of the polypeptide in a suitable expression host.

28. A recombinant expression vector comprising the nucleic acid construct of claim 27.

29. A cell comprising the nucleic acid construct of claim 27.

30. A method for producing a polypeptide having protein disulfide isomerase activity, comprising (a) cultivating a cell of claim 29; and (b) recovering the polypeptide.

* * * * *